(12) United States Patent
Teller et al.

(10) Patent No.: US 7,261,690 B2
(45) Date of Patent: *Aug. 28, 2007

(54) APPARATUS FOR MONITORING HEALTH, WELLNESS AND FITNESS

(75) Inventors: Eric Teller, Pittsburgh, PA (US); John M. Stivoric, Pittsburgh, PA (US); Christopher D. Kasabach, Pittsburgh, PA (US); Christopher D. Pacione, Pittsburgh, PA (US); John L. Moss, Monroeville, PA (US); Craig B. Liden, Sewickley, PA (US)

(73) Assignee: BodyMedia, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/923,181

(22) Filed: Aug. 6, 2001

(65) Prior Publication Data

US 2002/0019586 A1    Feb. 14, 2002

Related U.S. Application Data

(63) Continuation-in-part of application No. 09/602,537, filed on Jun. 23, 2000, now Pat. No. 6,605,038, which is a continuation-in-part of application No. 09/595,660, filed on Jun. 16, 2000.

(51) Int. Cl.
*A61B 5/00* (2006.01)
(52) U.S. Cl. ............... 600/300; 128/905; 128/920
(58) Field of Classification Search ........ 600/300–301; 128/903–904, 920; 705/2, 3; 340/573.1
See application file for complete search history.

(56) References Cited

U.S. PATENT DOCUMENTS 4,031,365 A   6/1977   Raggiotti et al.
4,052,979 A   10/1977  Scherr et al.

(Continued)

FOREIGN PATENT DOCUMENTS

DE    198 32 361 A1    2/2000

(Continued)

OTHER PUBLICATIONS

"Georgia Tech Researchers Develop First 'Smart T-shirt'," Nov. 14, 1997 press release, Georgia Institute of Technology.

(Continued)

*Primary Examiner*—Max F. Hindenburg
*Assistant Examiner*—Michael C Astorino
(74) *Attorney, Agent, or Firm*—Metz Lewis LLC; Barry I. Friedman

(57) ABSTRACT

A detecting, monitoring and reporting apparatus includes at least two sensors for facilitating the generation of data indicative of physiological parameters of the individual and/or data indicative of a contextual parameters of the individual. A processor is coupled to the sensors and is adapted to generate at least one of derived data from at least a portion of the data indicative of physiological parameters and analytical status data from at least a portion of at least one of the data indicative of physiological parameters, the data indicative of contextual parameters, the derived data and the analytical status data. A memory retrievably stores the data and one of various ways of transmitting the data is provided.

146 Claims, 18 Drawing Sheets

U.S. PATENT DOCUMENTS

| | | |
|---|---|---|
| 4,129,125 A | 12/1978 | Lester et al. |
| 4,148,304 A | 4/1979 | Mull |
| 4,151,831 A | 5/1979 | Lester |
| 4,192,000 A | 3/1980 | Lipsey |
| 4,364,398 A | 12/1982 | Sassi et al. |
| 4,377,171 A | 3/1983 | Wada |
| 4,407,295 A | 10/1983 | Steuer et al. |
| 4,488,558 A | 12/1984 | Simbruner et al. |
| 4,509,531 A | 4/1985 | Ward |
| 4,531,527 A | 7/1985 | Reinhold, Jr. et al. |
| 4,539,994 A | 9/1985 | Baumbach et al. |
| 4,557,273 A | 12/1985 | Stoller et al. |
| 4,608,987 A | 9/1986 | Mills |
| 4,622,979 A | 11/1986 | Katchis et al. |
| 4,672,977 A | 6/1987 | Kroll |
| 4,676,254 A | 6/1987 | Frohn |
| 4,757,453 A | 7/1988 | Nasiff |
| RE32,758 E | 10/1988 | Zartman |
| 4,784,162 A | 11/1988 | Ricks et al. |
| 4,803,625 A | 2/1989 | Fu et al. |
| 4,819,860 A | 4/1989 | Hargrove et al. |
| 4,827,943 A | 5/1989 | Bornn et al. |
| 4,828,257 A | 5/1989 | Dyer et al. |
| 4,883,063 A | 11/1989 | Bernard et al. |
| 4,891,756 A | 1/1990 | Williams, III |
| 4,917,108 A | 4/1990 | Mault |
| 4,958,645 A | 9/1990 | Cadell et al. |
| 4,966,154 A | 10/1990 | Cooper et al. |
| 4,981,139 A | 1/1991 | Pfohl |
| 5,007,427 A | 4/1991 | Suzuki et al. |
| 5,012,411 A | 4/1991 | Policastro et al. |
| 5,027,824 A | 7/1991 | Dougherty et al. |
| 5,038,792 A | 8/1991 | Mault |
| 5,040,541 A | 8/1991 | Poppendiek |
| 5,050,612 A | 9/1991 | Matsumura |
| 5,072,458 A | 12/1991 | Suzuki |
| 5,111,818 A | 5/1992 | Suzuki et al. |
| 5,135,311 A | 8/1992 | Alpert |
| 5,148,002 A | 9/1992 | Kuo et al. |
| 5,178,155 A | 1/1993 | Mault |
| 5,179,958 A | 1/1993 | Mault |
| 5,216,599 A | 6/1993 | Uebe et al. |
| 5,224,479 A | 7/1993 | Sekine |
| 5,263,491 A | 11/1993 | Thornton |
| 5,285,398 A | 2/1994 | Janik |
| 5,305,244 A | 4/1994 | Newman et al. |
| 5,335,664 A | 8/1994 | Nagashima |
| 5,353,793 A | 10/1994 | Bornn |
| 5,410,471 A | 4/1995 | Alyfuku et al. |
| 5,435,315 A | 7/1995 | McPhee et al. |
| 5,445,149 A | 8/1995 | Rotolo et al. |
| 5,458,123 A | 10/1995 | Unger |
| 5,474,090 A | 12/1995 | Begun et al. |
| 5,476,103 A | 12/1995 | Nashner |
| 5,484,389 A | 1/1996 | Stark et al. |
| 5,491,651 A | 2/1996 | Janik |
| 5,511,553 A | 4/1996 | Segalowitz |
| 5,515,858 A | 5/1996 | Myllymaki |
| 5,515,865 A | 5/1996 | Scanlon |
| 5,524,618 A | 6/1996 | Pottgen et al. |
| 5,555,490 A | 9/1996 | Carroll |
| 5,559,497 A | 9/1996 | Hong |
| 5,566,679 A | 10/1996 | Herriott |
| 5,581,238 A | 12/1996 | Chang et al. |
| 5,581,492 A | 12/1996 | Janik |
| 5,583,758 A | 12/1996 | McIlroy et al. |
| 5,611,085 A | 3/1997 | Rasmussen |
| 5,617,477 A | 4/1997 | Boyden |
| 5,622,180 A | 4/1997 | Tammi et al. |
| 5,645,068 A | 7/1997 | Mezack et al. |
| 5,663,703 A * | 9/1997 | Pearlman et al. ........ 340/573.1 |
| 5,666,096 A | 9/1997 | Van Zeeland |
| 5,670,944 A | 9/1997 | Myllymaki |
| 5,673,691 A | 10/1997 | Abrams et al. |
| 5,673,692 A | 10/1997 | Schulze et al. |
| 5,686,516 A | 11/1997 | Tzur |
| 5,687,734 A | 11/1997 | Dempsey et al. |
| 5,697,791 A | 12/1997 | Nashner et al. |
| 5,704,350 A | 1/1998 | Williams, III |
| 5,719,743 A | 2/1998 | Jenkins et al. |
| 5,724,025 A | 3/1998 | Tavori |
| 5,726,631 A | 3/1998 | Lin |
| 5,730,140 A | 3/1998 | Fitch |
| 5,738,104 A | 4/1998 | Lo et al. |
| 5,741,217 A | 4/1998 | Gero |
| 5,752,976 A | 5/1998 | Duffin et al. |
| 5,771,001 A | 6/1998 | Cobb |
| 5,778,882 A | 7/1998 | Raymond et al. |
| 5,798,907 A | 8/1998 | Janik |
| 5,803,915 A | 9/1998 | Kremenchugsky et al. |
| 5,813,766 A | 9/1998 | Chen |
| 5,813,994 A | 9/1998 | Pottgen et al. |
| 5,823,975 A | 10/1998 | Stark et al. |
| 5,827,180 A | 10/1998 | Goodman |
| 5,828,943 A | 10/1998 | Brown |
| 5,832,296 A | 11/1998 | Wang et al. |
| 5,832,448 A | 11/1998 | Brown |
| 5,836,300 A | 11/1998 | Mault |
| 5,853,005 A | 12/1998 | Scanlon |
| 5,855,550 A | 1/1999 | Lai et al. |
| 5,857,939 A | 1/1999 | Kaufman |
| 5,857,967 A | 1/1999 | Frid et al. |
| 5,862,803 A | 1/1999 | Besson et al. |
| 5,865,733 A | 2/1999 | Malinouskas et al. |
| 5,868,669 A | 2/1999 | Iliff |
| 5,868,671 A | 2/1999 | Mahoney |
| 5,871,451 A | 2/1999 | Unger et al. |
| 5,876,350 A | 3/1999 | Lo et al. |
| 5,879,163 A | 3/1999 | Brown et al. |
| 5,879,309 A | 3/1999 | Johnson et al. |
| 5,884,198 A | 3/1999 | Kese et al. |
| 5,888,172 A | 3/1999 | Andrus et al. |
| 5,897,493 A | 4/1999 | Brown |
| 5,899,855 A | 5/1999 | Brown |
| 5,902,250 A | 5/1999 | Verrier et al. |
| 5,908,396 A | 6/1999 | Hayakawa et al. |
| 5,912,865 A | 6/1999 | Ortega |
| 5,913,310 A | 6/1999 | Brown |
| 5,919,141 A | 7/1999 | Money et al. |
| 5,929,782 A | 7/1999 | Stark et al. |
| 5,933,136 A | 8/1999 | Brown |
| 5,941,837 A | 8/1999 | Amano et al. |
| 5,951,300 A | 9/1999 | Brown |
| 5,956,501 A | 9/1999 | Brown |
| 5,959,611 A | 9/1999 | Smailagic et al. |
| 5,960,403 A | 9/1999 | Brown |
| 5,976,083 A | 11/1999 | Richardson et al. |
| 6,032,119 A | 2/2000 | Brown et al. |
| 6,047,203 A | 4/2000 | Sackner et al. |
| 6,053,872 A | 4/2000 | Mohler |
| 6,059,692 A | 5/2000 | Hickman |
| 6,067,468 A | 5/2000 | Korenman et al. |
| 6,091,973 A | 7/2000 | Colla et al. |
| 6,101,407 A | 8/2000 | Groezinger |
| 6,101,478 A | 8/2000 | Brown |
| 6,135,107 A | 10/2000 | Mault |
| 6,138,079 A | 10/2000 | Putnam |
| 6,154,668 A | 11/2000 | Pedersen et al. |
| 6,168,563 B1 | 1/2001 | Brown |
| 6,184,797 B1 | 2/2001 | Stark et al. |
| 6,198,394 B1 | 3/2001 | Jacobsen et al. |
| 6,208,900 B1 | 3/2001 | Ecker et al. |
| 6,225,901 B1 | 5/2001 | Kail, IV |
| 6,225,980 B1 | 5/2001 | Weiss et al. |

| | | |
|---|---|---|
| 6,247,647 B1 | 6/2001 | Courtney et al. |
| 6,248,065 B1 | 6/2001 | Brown |
| 6,251,048 B1 | 6/2001 | Kaufman |
| 6,265,978 B1 | 7/2001 | Atlas |
| 6,285,897 B1 | 9/2001 | Kilcoyne et al. |
| 6,290,646 B1 | 9/2001 | Cosentino et al. |
| 6,290,650 B1 | 9/2001 | Butterfield et al. |
| 6,292,698 B1 | 9/2001 | Duffin et al. |
| 6,298,218 B1 | 10/2001 | Lowe et al. |
| 6,306,088 B1 | 10/2001 | Krausman et al. |
| 6,312,363 B1 | 11/2001 | Watterson et al. |
| 6,315,719 B1 | 11/2001 | Rode et al. |
| 6,336,900 B1 | 1/2002 | Alleckson et al. |
| 6,339,720 B1 | 1/2002 | Anzellini et al. |
| 6,341,229 B1 | 1/2002 | Akiva |
| 6,364,834 B1 | 4/2002 | Reuss et al. |
| 6,366,871 B1 | 4/2002 | Geva |
| 6,368,287 B1 | 4/2002 | Hadas |
| 6,371,123 B1 | 4/2002 | Stark et al. |
| 6,377,162 B1 | 4/2002 | Delestienne et al. |
| 6,385,473 B1 | 5/2002 | Haines et al. |
| 6,416,471 B1 | 7/2002 | Kumar et al. |
| 6,450,922 B1 | 9/2002 | Henderson et al. |
| 6,450,953 B1 | 9/2002 | Place et al. |
| 6,454,708 B1 | 9/2002 | Ferguson et al. |
| 6,466,232 B1 | 10/2002 | Newell et al. |
| 6,468,222 B1 | 10/2002 | Mault et al. |
| 6,478,736 B1 | 11/2002 | Mault |
| 6,494,829 B1 | 12/2002 | New, Jr. et al. |
| 6,513,532 B2 | 2/2003 | Mault et al. |
| 6,527,711 B1 | 3/2003 | Stivoric et al. |
| 6,532,381 B2 | 3/2003 | Bayer et al. |
| 6,547,745 B1 | 4/2003 | Rubinstein |
| 6,551,251 B2 | 4/2003 | Zuckerwar et al. |
| 6,553,251 B1 | 4/2003 | Lahdesmaki |
| 6,571,200 B1 | 5/2003 | Mault |
| 6,579,231 B1 * | 6/2003 | Phipps ..................... 600/300 |
| 6,584,344 B2 | 6/2003 | Hannula |
| 6,595,929 B2 | 7/2003 | Stivoric et al. |
| 6,597,944 B1 | 7/2003 | Hadas |
| 6,605,038 B1 | 8/2003 | Teller et al. |
| 6,610,012 B2 | 8/2003 | Mault |
| 6,656,125 B2 | 12/2003 | Misczynski et al. |
| 6,665,559 B2 | 12/2003 | Rowlandson |
| 6,690,959 B2 | 2/2004 | Thompson |
| 6,712,615 B2 | 3/2004 | Martin |
| 6,734,802 B2 | 5/2004 | Halleck et al. |
| 6,755,795 B2 | 6/2004 | Marmaropoulos et al. |
| 6,790,178 B1 | 9/2004 | Mault et al. |
| 6,808,473 B2 | 10/2004 | Hisano |
| 6,842,877 B2 | 1/2005 | Robarts et al. |
| 6,852,085 B2 | 2/2005 | Rubinstein |
| 6,874,127 B2 | 3/2005 | Newell et al. |
| 6,920,348 B2 | 7/2005 | Vasin et al. |
| 2001/0029340 A1 | 10/2001 | Mault et al. |
| 2001/0032059 A1 | 10/2001 | Kelly, Jr. et al. |
| 2001/0044581 A1 | 11/2001 | Mault |
| 2001/0049470 A1 | 12/2001 | Mault et al. |
| 2001/0056229 A1 | 12/2001 | Cosentino et al. |
| 2002/0019296 A1 | 2/2002 | Freeman et al. |
| 2002/0028995 A1 | 3/2002 | Mault |
| 2002/0032386 A1 | 3/2002 | Sackner et al. |
| 2002/0107450 A1 | 8/2002 | Ogura |
| 2002/0111539 A1 | 8/2002 | Cosentino et al. |
| 2002/0128804 A1 | 9/2002 | Geva |
| 2002/0133378 A1 | 9/2002 | Mault et al. |
| 2003/0055460 A1 | 3/2003 | Owen et al. |
| 2003/0069510 A1 | 4/2003 | Semler |
| 2003/0083559 A1 | 5/2003 | Thompson |

FOREIGN PATENT DOCUMENTS

| | | |
|---|---|---|
| DE | 19917666 A1 | 9/2000 |
| EP | 0 670 064 B1 | 11/1993 |
| EP | 0 707 825 A2 | 4/1996 |
| GB | 2322952 A | 5/1997 |
| WO | WO 93/01574 | 7/1992 |
| WO | WO 94/25841 | 4/1994 |
| WO | WO 97/06499 | 8/1996 |
| WO | WO 99/27483 | 6/1999 |
| WO | WO 00/11578 | 8/1999 |
| WO | WO 00/26822 | 10/1999 |
| WO | WO 00/32098 | 11/1999 |
| WO | 01/08554 | 2/2000 |
| WO | 00/52604 | 3/2000 |
| WO | 00/47108 | 8/2000 |
| WO | 00/51543 | 9/2000 |
| WO | 01/28416 | 9/2000 |
| WO | 01/26535 | 10/2000 |
| WO | 01/26547 | 10/2000 |
| WO | 01/28495 | 10/2000 |
| WO | 01/39089 | 11/2000 |
| WO | 01/52718 | 1/2001 |
| WO | 01/56454 | 2/2001 |
| WO | 01/82783 | 4/2001 |
| WO | 01/82789 | 5/2001 |
| WO | 01/89365 | 5/2001 |
| WO | 01/89368 | 5/2001 |
| WO | 02/69798 | 9/2002 |

OTHER PUBLICATIONS

"Personal Health Monitor for Homes," Timo Tuomisto and Vesa Pentikainen, ERCIM News, No. 29, Apr. 1997.

"CYBeR-CARE Announces U.S. Patent Office Allows 25 Additional Claims for its Internet Healthcare Technologies," *BW HealthWire*, Oct. 7, 1999.

"Nearer to the Heart," Briana Krebs, *Washington Post*, Jan. 17, 1999.

"Portable Sensor Provides Remote Monitoring of Heart," *Nikkie Weekly*, Oct. 27, 1998.

"FDA Clears New Datex-Ohmeda 3900/3900P Pulse Oximeter with World's First Remote Fax Capability," *BW HealthWire*, Dec. 3, 1998.

"Estee Soft Announces New Version of LifeConnect, Providing Advanced Telemonitoring Capabilities for the Mobile Practioner," *Business Wire*, Jan. 20, 1999.

"Matsushita Electric Works to Sell Home Health Check System," *The Nihon Keizai Shimbun*, Dec. 17, 1998.

Thermal Gap Fillers, Kent Young, Feb. 6, 2001 (article downloaded from www.chomerics.com) THERM-A-GAP, Chomerics Technical Bulletin 70, Feb. 6, 2001.

CoolPoly, the Original Thermally Conductive Polymer, Feb. 7, 2001 (article downloaded from www.coolpolymers.com) Micro-Foil Heat Flux Sensors, RdF Corporation Catalog No. HFS-A, Mar. 1998.

Industrial Micro-Foil Heat Flux Sensor, RdF Corporation Datasheet No. HFS-B, Oct. 1995 Industrial/Commercial Micro-Foil Heat Flux Sensor, RdF Corporation Catalong No. HFS-C, Dec. 1999.

Weight Watchers TurnAround, Weight Watchers, 2004 (downloaded from www.weightwatchers.com) Weight Loss Programs, Jenny Craig, 2004 (downloaded from www.jennycraig.com).

The Complete Nutrition & Weight Management Solution Based on Your Unique Metabolic Fingerpring & Goals, BalanceLog, 2004 (downloaded from www.healthetech.com) What is FitDay?, FitDay, 2004 (downloaded from www.fitday.com).

"A combined heart rate and movement sensor: proof of concept and preliminary testing study," K. Rennie, T. Rowsell, S.A. Jebb, D. Holburn & N.J. Wareham, 2000.

"Ironman Speed and Distance System" (downloaded from www.timex.com), Timex, Oct. 4, 2002.

"Ironman Speed Distance System—Once Again Timex Revolutionizes the Sportwatch" (downloaded from www.timex.com), Timex, Jan. 8, 2002.

Polar M91ti Heart Rate Monitor Users Manual—Quick Guide, Polar Electro Inc., Nov. 2000.

Polar USA—Product Detail—M91ti (downloaded from www.polarusa.com), Polar USA, Oct. 4, 2002.

Warfighter Physiological Status Monitoring, 1999 MOMRP Fact Sheet No. 6, USAMRMC Military Operational Medicine Research Program. [Retrieved from Internet. URL : <http://www.momrp.org/publications/WPSM.pdf>.

Henshaw, D., The H.J. Andrews Climatological Field Measurement Program, Aug. 9, 1997. [Retrieved from Internet. URL ; <http://www.fsl.orst.edu/lter/research/component/climate/summary.cfm?sum=clim97&topnav=57>.

* cited by examiner

APPARATUS FOR MONITORING HEALTH, WELLNESS AND FITNESS

CROSS REFERENCE TO A RELATED APPLICATION

This application is a continuation-in-part of U.S. application Ser. No. 09/602,537, filed on Jun. 23, 2000, now U.S. Pat. No. 6,605,038, which is a continuation-in-part of U.S. application Ser. No. 09/595,660, filed on Jun. 16, 2000.

FIELD OF THE INVENTION

The present invention relates to a system for monitoring health, wellness and fitness, and in particular, to a system for collecting, using a sensor device, and storing at a remote site data relating to an individual's physiological state, lifestyle, and various contextual parameters, and making such data and analytical information based on such data available to the individual, preferably over an electronic network. In addition, the present invention also relates to an apparatus for monitoring health, wellness and fitness, and in particular, to an apparatus including one or more sensors for collecting and storing data relating to an individual's physiological state and various contextual parameters, and making such data and analytical information based on such data available to the individual.

BACKGROUND OF THE INVENTION

Research has shown that a large number of the top health problems in society are either caused in whole or in part by an unhealthy lifestyle. More and more, our society requires people to lead fast-paced, achievement-oriented lifestyles that often result in poor eating habits, high stress levels, lack of exercise, poor sleep habits and the inability to find the time to center the mind and relax. Recognizing this fact, people are becoming increasingly interested in establishing a healthier lifestyle.

Traditional medicine, embodied in the form of an HMO or similar organizations, does not have the time, the training, or the reimbursement mechanism to address the needs of those individuals interested in a healthier lifestyle. There have been several attempts to meet the needs of these individuals, including a perfusion of fitness programs and exercise equipment, dietary plans, self-help books, alternative therapies, and most recently, a plethora of health information web sites on the Internet. Each of these attempts are targeted to empower the individual to take charge and get healthy. Each of these attempts, however, addresses only part of the needs of individuals seeking a healthier lifestyle and ignores many of the real barriers that most individuals face when trying to adopt a healthier lifestyle. These barriers include the fact that the individual is often left to himself or herself to find motivation, to implement a plan for achieving a healthier lifestyle, to monitor progress, and to brainstorm solutions when problems arise; the fact that existing programs are directed to only certain aspects of a healthier lifestyle, and rarely come as a complete package; and the fact that recommendations are often not targeted to the unique characteristics of the individual or his life circumstances.

SUMMARY OF THE INVENTION

A system is disclosed for detecting, monitoring and reporting human physiological information. The system includes a sensor device which generates at least one of data indicative of one or more physiological parameters and derived data from at least a portion of the data indicative of one or more physiological parameters when placed in proximity with at least a portion of the human body. The system also includes a central monitoring unit located remote from the sensor device. The central monitoring unit generates analytical status data from at least one of the data indicative of one or more physiological parameters, the derived data, and analytical status data that has previously been generated. The central monitoring unit also includes a data storage device for retrievably storing the data it receives and generates. The disclosed system also includes means for establishing electronic communication between the sensor device and the central monitoring unit. Examples may include various known types of long range wireless transmission devices, or a physical or a short range wireless coupling to a computer which in turn establishes electronic communication with the central monitoring unit over an electronic network such as the Internet. Also included in the system is a means for transmitting the data indicative of one or more physiological parameters, the derived data, and/or the analytical status data to a recipient, such as the individual or a third party authorized by the individual.

Also disclosed is a method of detecting, monitoring and reporting human physiological information. The method includes generating at least one of data indicative of one or more physiological parameters of an individual and derived data from at least a portion of the data indicative of one or more physiological parameters using a sensor device adapted to be placed in proximity with at least a portion of the human body. The at least one of the data indicative of one or more physiological parameters and the derived data are transmitted to a central monitoring unit remote from said sensor device and retrievably stored in a storage device. Analytical status data is generated from at least a portion of at least one of the data indicative of one or more physiological parameters, the derived data and the analytical status data, and at least one of the data indicative of one or more physiological parameters, the derived data and the analytical status data is transmitted to a recipient.

The sensor device includes one or more sensors for generating signals in response to physiological characteristics of the individual. The sensor device may also include a processor that is adapted to generate the data indicative of one or more physiological parameters from the signals generated by the one or more sensors. The processor may also be adapted to generate the derived data. Alternatively, the derived data may be generated by the central monitoring unit.

The central monitoring unit may be adapted to generate one or more web pages containing the data indicative of one or more physiological parameters, the derived data, and/or the analytical status data. The web pages generated by the central monitoring unit are accessible by the recipient over an electronic network, such as the Internet. Alternatively, the data indicative of one or more physiological parameters, the derived data, and/or the analytical status data may be transmitted to the recipient in a physical form such as mail or facsimile.

The system and method may also obtain life activities data of the individual and may use such life activities data when generating the analytical status data. Furthermore, the sensor device may also be adapted to generate data indicative of one or more contextual parameters of the individual. The system and method may then use the data indicative of one or more contextual parameters when generating the analytical status data.

Also disclosed is a system for monitoring the degree to which an individual has followed a predetermined routine. The system includes a sensor device adapted to generate at least one of data indicative of one or more physiological parameters of the individual and derived data from at least a portion of the data indicative of one or more physiological parameters when the sensor device is placed in proximity with at least a portion of the human body. Also included is a means for transmitting the data that is generated by the sensor device to a central monitoring unit remote from the sensor device and means for providing life activities data of the individual to the central monitoring unit. The central monitoring unit is adapted to generate and provide feedback to a recipient relating to the degree to which the individual has followed the predetermined routine. The feedback is generated from at least a portion of at least one of the data indicative of one or more physiological parameters, the derived data, and the life activities data.

Also disclosed is a method of monitoring the degree to which an individual has followed a predetermined routine. The method includes receiving, at a central monitoring unit, at least one of data indicative of one or more physiological parameters of said individual and derived data based on at least a portion of the data indicative of one or more physiological parameters, wherein the data indicative of one or more physiological parameters and the derived data are generated by a sensor device when placed in proximity with at least a portion of the human body. Also received at the central monitoring unit is life activities data of the individual. The method further includes generating at the central monitoring unit feedback relating to the degree to which the individual has followed the predetermined routine, the feedback being generated from at least a portion of at least one of the data indicative of one or more physiological parameters of the individual, the derived data, and the life activities data, and providing the feedback to a recipient.

The predetermined routine may include a plurality of categories, wherein the feedback is generated and provided with respect to each of the categories. Examples of the categories include nutrition, activity level, mind centering, sleep, and daily activities. The feedback maybe provided in graphical or textual form and may be contained in one or more web pages generated by the central monitoring unit. Alternatively, the feedback may be transmitted to the recipient in a physical form.

An alternate system for detecting, monitoring and reporting human physiological information is also disclosed. The system includes a sensor device adapted to be placed in contact with an individual's upper arm. The sensor device includes at least one of an accelerometer, a GSR sensor and a heat flux sensor and is adapted to generate data indicative of at least one of activity, galvanic skin response, and heat flow of the individual wearing the sensor device. The sensor device may also be adapted to generate derived data from at least a portion of the data indicative of at least one of activity, galvanic skin response and heat flow. The sensor device may include a computer housing and a flexible wing body having first and second wings adapted to wrap around a portion of the individual's arm. The sensor device may also be adapted to provide audible, visible or tactile feedback to the wearer.

The system also includes a central monitoring unit located remote from the sensor device. The central monitoring unit generates analytical status data from at least one of the data indicative of at least one of activity, galvanic skin response and heat flow, the derived data, and analytical status data that has previously been generated. The central monitoring unit may also be adapted to generate derived data from the data indicative of at least one of activity, galvanic skin response and heat flow. The central monitoring unit also includes a data storage device for retrievably storing the data it receives and generates. The disclosed system also includes means for establishing electronic communication between the sensor device and the central monitoring unit. Also included in the system is a means for transmitting the data indicative of at least one of activity, galvanic skin response and heat flow, the derived data, and/or the analytical status data to a recipient, such as the individual or a third party authorized by the individual.

The central monitoring unit may be adapted to generate one or more web pages containing the data indicative of at least one of activity, galvanic skin response and heat flow, the derived data, and/or the analytical status data. The web pages generated by the central monitoring unit are accessible by the recipient over an electronic network, such as the Internet. Alternatively, the data indicative of at least one of activity, galvanic skin response and heat flow, the derived data, and/or the analytical status data may be transmitted to the recipient in a physical form such as mail or facsimile.

The system may also obtain life activities data of the individual and may use such life activities data when generating the analytical status data. Furthermore, the sensor device may also be adapted to generate data indicative of one or more contextual parameters of the individual. The system may then use the data indicative of one or more contextual parameters when generating the analytical status data.

Also disclosed is an alternate system for monitoring the degree to which an individual has followed a suggested routine. The system includes a sensor device as described above. Also included is a means for transmitting the data that is generated by the sensor device to a central monitoring unit remote from the sensor device and means for providing life activities data of the individual to the central monitoring unit. The central monitoring unit is adapted to generate and provide feedback to a recipient relating to the degree to which the individual has followed the suggested routine. The feedback is generated from at least a portion of at least one of the data indicative of at least one of activity, galvanic skin response and heat flow, the derived data, and the life activities data.

The suggested routine may include a plurality of categories, wherein the feedback is generated and provided with respect to each of the categories. Examples of the categories include nutrition, activity level, mind centering, sleep, and daily activities. The feedback may be provided in graphical or textual form and may be contained in one or more web pages generated by the central monitoring unit. Alternatively, the feedback may be transmitted to the recipient in a physical form.

According to an alternate embodiment of the present invention, an apparatus for detecting, monitoring and reporting at least one of human physiological and contextual information is disclosed which includes at least two sensors selected from the group consisting of physiological sensors and contextual sensors. The physiological sensors are adapted to facilitate the generation of data indicative of one or more physiological parameters of an individual, and the contextual sensors are adapted to facilitate the generation of data indicative of one or more contextual parameters of the individual. A processor is coupled to the sensors and is adapted to generate at least one of derived data from at least a portion of the data indicative of physiological parameters and analytical status data from at least a portion of at least one of the data indicative of physiological parameters, the data indicative of contextual parameters, the derived data and the analytical status data. A memory is provided for retrievably storing at least one of the data indicative of physiological parameters, the data indicative of contextual parameters, the derived data and the analytical status data. Various options are available for transmitting to the individual at least one of the data indicative of physiological parameters, the data indicative of contextual parameters, the derived data and the analytical status data, including a visual output device, a tactile output device, an audible output device, and a computing device coupled to the apparatus. The apparatus may also include a component to enable the manual entry of information, and a wireless device to enable the apparatus to receive information from and/or output information to at least one of a wireless device worn by the individual, a wireless device implanted in the body of the individual, and a wireless device located near the individual.

According to a further alternate embodiment of the present invention, an apparatus for detecting, monitoring and reporting at least one of human physiological and contextual information is disclosed that includes a sensor device and a computing device coupled to the sensor device. The sensor device includes at least two sensors selected from the group consisting of physiological sensors and contextual sensors. The physiological sensors are adapted to facilitate the generation of data indicative of one or more physiological parameters of an individual, and the contextual sensors are adapted to facilitate the generation of data indicative of one or more contextual parameters of the individual. The sensor device also includes a memory for retrievably storing at least one of the data indicative of physiological parameters and the data indicative of contextual parameters. The computing device is adapted to generate at least one of derived data from at least a portion of the data indicative of physiological parameters and analytical status data from at least a portion of at least one of the data indicative of physiological parameters, the data indicative of contextual parameters, the derived data and the analytical status data. Various options are available for transmitting to the individual at least one of the data indicative of physiological parameters, the data indicative of contextual parameters, the derived data and the analytical status data, including a visual output device, a tactile output device, an audible output device, and the computing device. The apparatus may also include a component to enable the manual entry of information, and a wireless device to enable the apparatus to receive information from and/or output information to at least one of a wireless device worn by the individual, a wireless device implanted in the body of the individual, and a wireless device located near the individual. As an alternative, the apparatus may include a processor adapted to generate derived data from at least a portion of the data indicative of physiological parameters.

According to a further alternate embodiment of the present invention, an apparatus for monitoring and reporting at least one of human physiological and contextual information and nutritional information is disclosed that includes at least two sensors selected from the group consisting of physiological sensors and contextual sensors. The physiological sensors are adapted to facilitate the generation of data indicative of one or more physiological parameters of an individual and the contextual sensors are adapted to facilitate the generation of data indicative of one or more contextual parameters of said individual. The apparatus also includes means for entering food consumption information into the apparatus. A memory for storing conversion information for converting the food consumption information into nutritional information is also provided. The apparatus further includes a processor adapted to generate at least one of derived data from at least a portion of the data indicative of physiological parameters and analytical status data from at least a portion of at least one of the data indicative of physiological parameters, the data indicative of contextual parameters, the derived data, the nutritional information and the analytical status data, and means for transmitting to the individual at least one of the data indicative of physiological parameters, the data indicative of contextual parameters, the derived data, and the analytical status data.

BRIEF DESCRIPTION OF THE DRAWINGS

Further features and advantages of the present invention will be apparent upon consideration of the following detailed description of the present invention, taken in conjunction with the following drawings, in which like reference characters refer to like parts, and in which.

DESCRIPTION OF THE PREFERRED EMBODIMENTS

Figure 1:
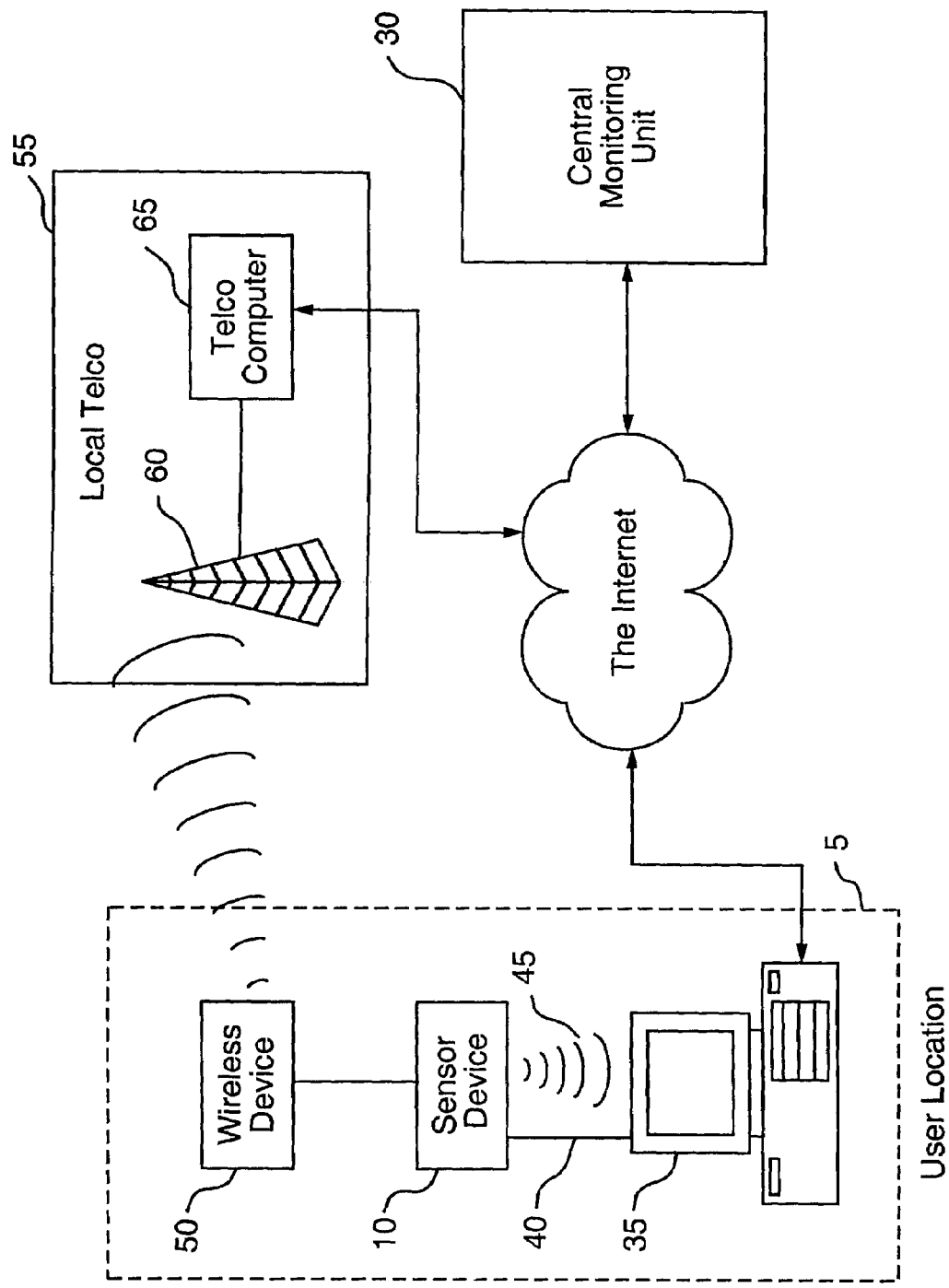
FIG. 1 is a diagram of an embodiment of a system for monitoring physiological data and lifestyle over an electronic network according to the present invention.

In general, according to the present invention, data relating to the physiological state, the lifestyle and certain contextual parameters of an individual is collected and transmitted, either subsequently or in real-time, to a site, preferably remote from the individual, where it is stored for later manipulation and presentation to a recipient, preferably over an electronic network such as the Internet. Contextual parameters as used herein means parameters relating to the environment, surroundings and location of the individual, including, but not limited to, air quality, sound quality, ambient temperature, global positioning and the like. Referring to FIG. 1, located at user location 5 is sensor device 10 adapted to be placed in proximity with at least a portion of the human body. Sensor device 10 is preferably worn by an individual user on his or her body, for example as part of a garment such as a form fitting shirt, or as part of an arm band or the like. Sensor device 10, includes one or more sensors, which are adapted to generate signals in response to physiological characteristics of an individual, and a microprocessor. Proximity as used herein means that the sensors of sensor device 10 are separated from the individual's body by a material or the like, or a distance such that the capabilities of the sensors are not impeded.

Sensor device 10 generates data indicative of various physiological parameters of an individual, such as the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and UV radiation exposure and absorption. In certain cases, the data indicative of the various physiological parameters is the signal or signals themselves generated by the one or more sensors and in certain other cases the data is calculated by the microprocessor based on the signal or signals generated by the one or more sensors. Methods for generating data indicative of various physiological parameters and sensors to be used therefor are well known. Table 1 provides several examples of such well known methods and shows the parameter in question, the method used, the sensor device used, and the signal that is generated. Table 1 also provides an indication as to whether further processing based on the generated signal is required to generate the data.

TABLE 1

| Parameter | Method | Sensor | Signal | Further Processing |
|---|---|---|---|---|
| Heart Rate | EKG | 2 Electrodes | DC Voltage | Yes |
| Pulse Rate | BVP | LED Emitter and Optical Sensor | Change in Resistance | Yes |
| Beat-to-Beat Variability | Heart Rate | 2 Electrodes | DC Voltage | Yes |

TABLE 1-continued

| Parameter | Method | Sensor | Signal | Further Processing |
|---|---|---|---|---|
| EKG | Skin Surface Potentials | 3-10 Electrodes | DC Voltage | No |
| Respiration Rate | Chest Volume Change | Strain Gauge | Change in Resistance | Yes |
| Skin Temperature | Surface Temperature Probe | Thermistors | Change in Resistance | Yes |
| Core Temperature | Esophageal or Rectal Probe | Thermistors | Change in Resistance | Yes |
| Heat Flow | Heat Flux | Thermopile | DC Voltage | Yes |
| Galvanic Skin Response | Skin Conductance | 2 Electrodes | Change in Resistance | No |
| EMG | Skin Surface Potentials | 3 Electrodes | DC Voltage | No |
| EEG | Skin Surface Potentials | Multiple Electrodes | DC Voltage | Yes |
| EOG | Eye Movement | Thin Film Piezoelectric Sensors | DC Voltage | Yes |
| Blood Pressure | Non-Invasive Korotkuff Sounds | Electronic Sphygromarometer | Change in Resistance | Yes |
| Body Fat | Body Impedance | 2 Active Electrodes | Change in Impedance | Yes |
| Activity in Interpreted G Shocks per Minute | Body Movement | Accelerometer | DC Voltage, Capacitance Changes | Yes |
| Oxygen Consumption | Oxygen Uptake | Electrochemical | DC Voltage Change | Yes |
| Glucose Level | Non-Invasive | Electrochemical | DC Voltage Change | Yes |
| Body Position (e.g. supine, erect, sitting) | N/A | Mercury Switch Array | DC Voltage Change | Yes |
| Muscle Pressure | N/A | Thin Film Piezoelectric Sensors | DC Voltage Change | Yes |
| UV Radiation Absorption | N/A | UV Sensitive Photo Cells | DC Voltage Change | Yes |

The types of data listed in Table 1 are intended to be examples of the types of data that can be generated by sensor device 10. It is to be understood that other types of data relating to other parameters can be generated by sensor device 10 without departing from the scope of the present invention.

The microprocessor of sensor device 10 may be programmed to summarize and analyze the data. For example, the microprocessor can be programmed to calculate an average, minimum or maximum heart rate or respiration rate over a defined period of time, such as ten minutes. Sensor device 10 may be able to derive information relating to an individual's physiological state based on the data indicative of one or more physiological parameters. The microprocessor of sensor device 10 is programmed to derive such information using known methods based on the data indicative of one or more physiological parameters. Table 2 provides examples of the type of information that can be derived, and indicates some of the types of data that can be used therefor.

TABLE 2

| Derived Information | Data Used |
| --- | --- |
| Ovulation | Skin temperature, core temperature, oxygen consumption |
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Calories burned | Heart rate, pulse rate, respiration rate, heat flow, activity, oxygen consumption |
| Basal metabolic rate | Heart rate, pulse rate, respiration rate, heat flow, activity, oxygen consumption |
| Basal temperature | Skin temperature, core temperature |
| Activity level | Heart rate, pulse rate, respiration rate, heat flow, activity, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |
| Relaxation level | EKG, beat-to-beat variability, heart rate, pulse rate, respiration rate, skin temperature, heat flow, galvanic skin response, EMG, EEG, blood pressure, activity, oxygen consumption |
| Maximum oxygen consumption rate | EKG, heart rate, pulse rate, respiration rate, heat flow, blood pressure, activity, oxygen consumption |
| Rise time or the time it takes to rise from a resting rate to 85% of a target maximum | Heart rate, pulse rate, heat flow, oxygen consumption |
| Time in zone or the time heart rate was above 85% of a target maximum | Heart rate, pulse rate, heat flow, oxygen consumption |
| Recovery time or the time it takes heart rate to return to a resting rate after heart rate was above 85% of a target maximum | Heart rate, pulse rate, heat flow, oxygen consumption |

Additionally, sensor device 10 may also generate data indicative of various contextual parameters relating to the environment surrounding the individual. For example, sensor device 10 can generate data indicative of the air quality, sound level/quality, light quality or ambient temperature near the individual, or even the global positioning of the individual. Sensor device 10 may include one or more sensors for generating signals in response to contextual characteristics relating to the environment surrounding the individual, the signals ultimately being used to generate the type of data described above. Such sensors are well known, as are methods for generating contextual parametric data such as air quality, sound level/quality, ambient temperature and global positioning.

Figure 2:
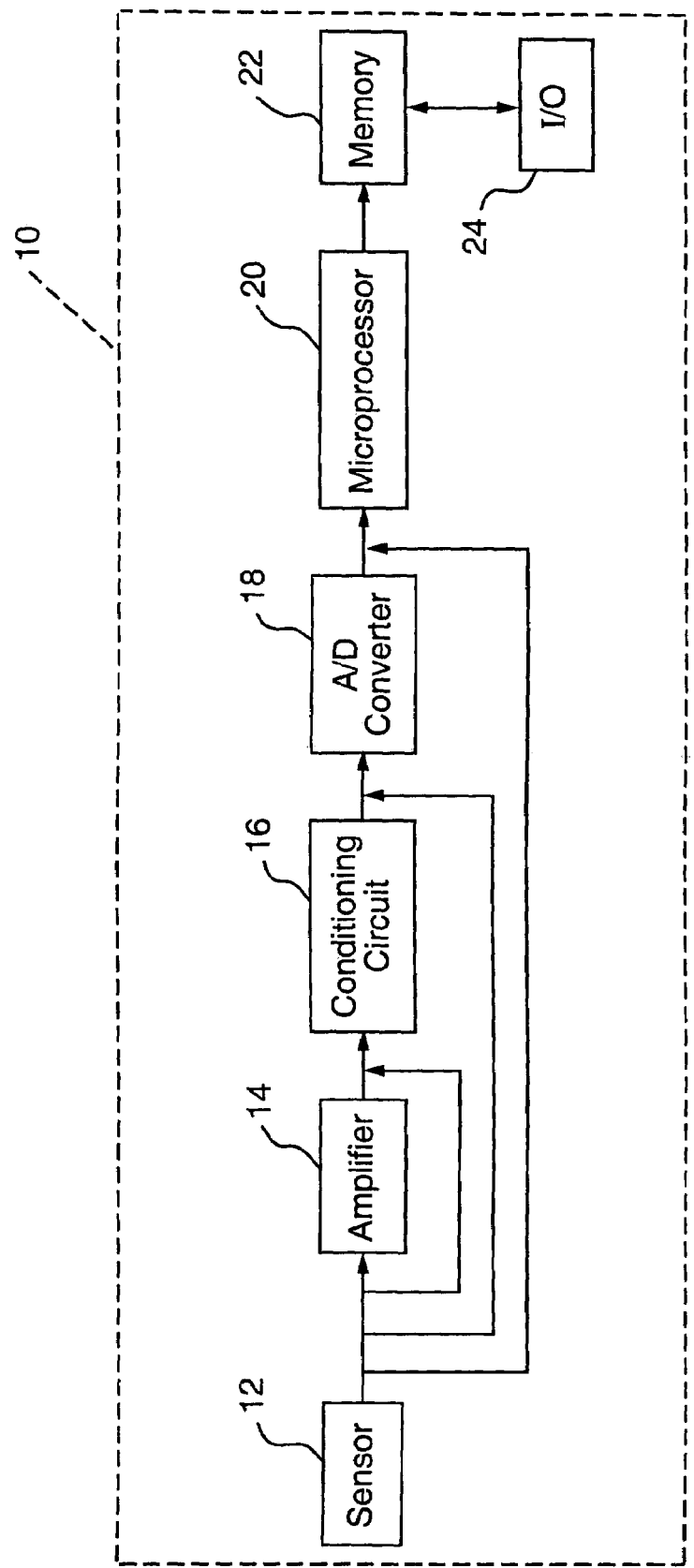
FIG. 2 is a block diagram of an embodiment of the sensor device shown in FIG. 1.

FIG. 2 is a block diagram of an embodiment of sensor device 10. Sensor device 10 includes at least one sensor 12 and microprocessor 20. Depending upon the nature of the signal generated by sensor 12, the signal can be sent through one or more of amplifier 14, conditioning circuit 16, and analog-to-digital converter 18, before being sent to microprocessor 20. For example, where sensor 12 generates an analog signal in need of amplification and filtering, that signal can be sent to amplifier 14, and then on to conditioning circuit 16, which may, for example, be a band pass filter. The amplified and conditioned analog signal can then be transferred to analog-to-digital converter 18, where it is converted to a digital signal. The digital signal is then sent to microprocessor 20. Alternatively, if sensor 12 generates a digital signal, that signal can be sent directly to microprocessor 20.

A digital signal or signals representing certain physiological and/or contextual characteristics of the individual user may be used by microprocessor 20 to calculate or generate data indicative of physiological and/or contextual parameters of the individual user. Microprocessor 20 is programmed to derive information relating to at least one aspect of the individual's physiological state. It should be understood that microprocessor 20 may also comprise other forms of processors or processing devices, such as a microcontroller, or any other device that can be programmed to perform the functionality described herein.

The data indicative of physiological and/or contextual parameters can, according to one embodiment of the present invention, be sent to memory 22, such as flash memory, where it is stored until uploaded in the manner to be described below. Although memory 22 is shown in FIG. 2 as a discrete element, it will be appreciated that it may also be part of microprocessor 20. Sensor device 10 also includes input/output circuitry 24, which is adapted to output and receive as input certain data signals in the manners to be described herein. Thus, memory 22 of the sensor device 10 will build up, over time, a store of data relating to the individual user's body and/or environment. That data is periodically uploaded from sensor device 10 and sent to remote central monitoring unit 30, as shown in FIG. 1, where it is stored in a database for subsequent processing and presentation to the user, preferably through a local or global electronic network such as the Internet. This uploading of data can be an automatic process that is initiated by sensor device 10 periodically or upon the happening of an event such as the detection by sensor device 10 of a heart rate below a certain level, or can be initiated by the individual user or some third party authorized by the user, preferably according to some periodic schedule, such as every day at 10:00 p.m. Alternatively, rather than storing data in memory 22, sensor device 10 may continuously upload data in real time.

The uploading of data from sensor device 10 to central monitoring unit 30 for storage can be accomplished in various ways. In one embodiment, the data collected by sensor device 10 is uploaded by first transferring the data to personal computer 35 shown in FIG. 1 by means of physical connection 40, which, for example, may be a serial connection such as an RS232 or USB port. This physical connection may also be accomplished by using a cradle, not shown, that is electronically coupled to personal computer 35 into which sensor device 10 can be inserted, as is common with many commercially available personal digital assistants. The uploading of data could be initiated by then pressing a button on the cradle or could be initiated automatically upon insertion of sensor device 10. The data collected by sensor device 10 may be uploaded by first transferring the data to personal computer 35 by means of short-range wireless transmission, such as infrared or RF transmission, as indicated at 45.

Once the data is received by personal computer 35, it is optionally compressed and encrypted by any one of a variety of well known methods and then sent out over a local or global electronic network, preferably the Internet, to central monitoring unit 30. It should be noted that personal computer 35 can be replaced by any computing device that has access to and that can transmit and receive data through the electronic network, such as, for example, a personal digital assistant such as the Palm VII sold by Palm, Inc., or the Blackberry 2-way pager sold by Research in Motion, Inc.

Alternatively, the data collected by sensor device 10, after being encrypted and, optionally, compressed by microprocessor 20, may be transferred to wireless device 50, such as a 2-way pager or cellular phone, for subsequent long distance wireless transmission to local telco site 55 using a wireless protocol such as e-mail or as ASCII or binary data. Local telco site 55 includes tower 60 that receives the wireless transmission from wireless device 50 and computer 65 connected to tower 60. According to the preferred embodiment, computer 65 has access to the relevant electronic network, such as the Internet, and is used to transmit the data received in the form of the wireless transmission to the central monitoring unit 30 over the Internet. Although wireless device 50 is shown in FIG. 1 as a discrete device coupled to sensor device 10, it or a device having the same or similar functionality may be embedded as part of sensor device 10.

Sensor device 10 may be provided with a button to be used to time stamp events such as time to bed, wake time, and time of meals. These time stamps are stored in sensor device 10 and are uploaded to central monitoring unit 30 with the rest of the data as described above. The time stamps may include a digitally recorded voice message that, after being uploaded to central monitoring unit 30, are translated using voice recognition technology into text or some other information format that can be used by central monitoring unit 30.

In addition to using sensor device 10 to automatically collect physiological data relating to an individual user, a kiosk could be adapted to collect such data by, for example, weighing the individual, providing a sensing device similar to sensor device 10 on which an individual places his or her hand or another part of his or her body, or by scanning the individual's body using, for example, laser technology or an iStat blood analyzer. The kiosk would be provided with processing capability as described herein and access to the relevant electronic network, and would thus be adapted to send the collected data to the central monitoring unit 30 through the electronic network. A desktop sensing device, again similar to sensor device 10, on which an individual places his or her hand or another part of his or her body may also be provided. For example, such a desktop sensing device could be a blood pressure monitor in which an individual places his or her arm. An individual might also wear a ring having a sensor device 10 incorporated therein. A base, not shown, could then be provided which is adapted to be coupled to the ring. The desktop sensing device or the base just described may then be coupled to a computer such as personal computer 35 by means of a physical or short range wireless connection so that the collected data could be uploaded to central monitoring unit 30 over the relevant electronic network in the manner described above. A mobile device such as, for example, a personal digital assistant, might also be provided with a sensor device 10 incorporated therein. Such a sensor device 10 would be adapted to collect data when mobile device is placed in proximity with the individual's body, such as by holding the device in the palm of one's hand, and upload the collected data to central monitoring unit 30 in any of the ways described herein.

Furthermore, in addition to collecting data by automatically sensing such data in the manners described above, individuals can also manually provide data relating to various life activities that is ultimately transferred to and stored at central monitoring unit 30. An individual user can access a web site maintained by central monitoring unit 30 and can directly input information relating to life activities by entering text freely, by responding to questions posed by the web site, or by clicking through dialog boxes provided by the web site. Central monitoring unit 30 can also be adapted to periodically send electronic mail messages containing questions designed to elicit information relating to life activities to personal computer 35 or to some other device that can receive electronic mail, such as a personal digital assistant, a pager, or a cellular phone. The individual would then provide data relating to life activities to central monitoring unit 30 by responding to the appropriate electronic mail message with the relevant data. Central monitoring unit 30 may also be adapted to place a telephone call to an individual user in which certain questions would be posed to the individual user. The user could respond to the questions by entering information using a telephone keypad, or by voice, in which case conventional voice recognition technology would be used by central monitoring unit 30 to receive and process the response. The telephone call may also be initiated by the user, in which case the user could speak to a person directly or enter information using the keypad or by voice/voice recognition technology. Central monitoring unit 30 may also be given access to a source of information controlled by the user, for example the user's electronic calendar such as that provided with the Outlook product sold by Microsoft Corporation of Redmond, Wash., from which it could automatically collect information. The data relating to life activities may relate to the eating, sleep, exercise, mind centering or relaxation, and/or daily living habits, patterns and/or activities of the individual. Thus, sample questions may include: What did you have for lunch today? What time did you go to sleep last night? What time did you wake up this morning? How long did you run on the treadmill today?

Feedback may also be provided to a user directly through sensor device 10 in a visual form, for example through an LED or LCD or by constructing sensor device 10, at least in part, of a thermochromatic plastic, in the form of an acoustic signal or in the form of tactile feedback such as vibration. Such feedback may be a reminder or an alert to eat a meal or take medication or a supplement such as a vitamin, to engage in an activity such as exercise or meditation, or to drink water when a state of dehydration is detected. Additionally, a reminder or alert can be issued in the event that a particular physiological parameter such as ovulation has been detected, a level of calories burned during a workout has been achieved or a high heart rate or respiration rate has been encountered.

As will be apparent to those of skill in the art, it may be possible to "download" data from central monitoring unit 30 to sensor device 10. The flow of data in such a download process would be substantially the reverse of that described above with respect to the upload of data from sensor device 10. Thus, it is possible that the firmware of microprocessor 20 of sensor device 10 can be updated or altered remotely, i.e., the microprocessor can be reprogrammed, by downloading new firmware to sensor device 10 from central monitoring unit 30 for such parameters as timing and sample rates of sensor device 10. Also, the reminders/alerts provided by sensor device 10 may be set by the user using the web site maintained by central monitoring unit 30 and subsequently downloaded to the sensor device 10.

Figure 3:
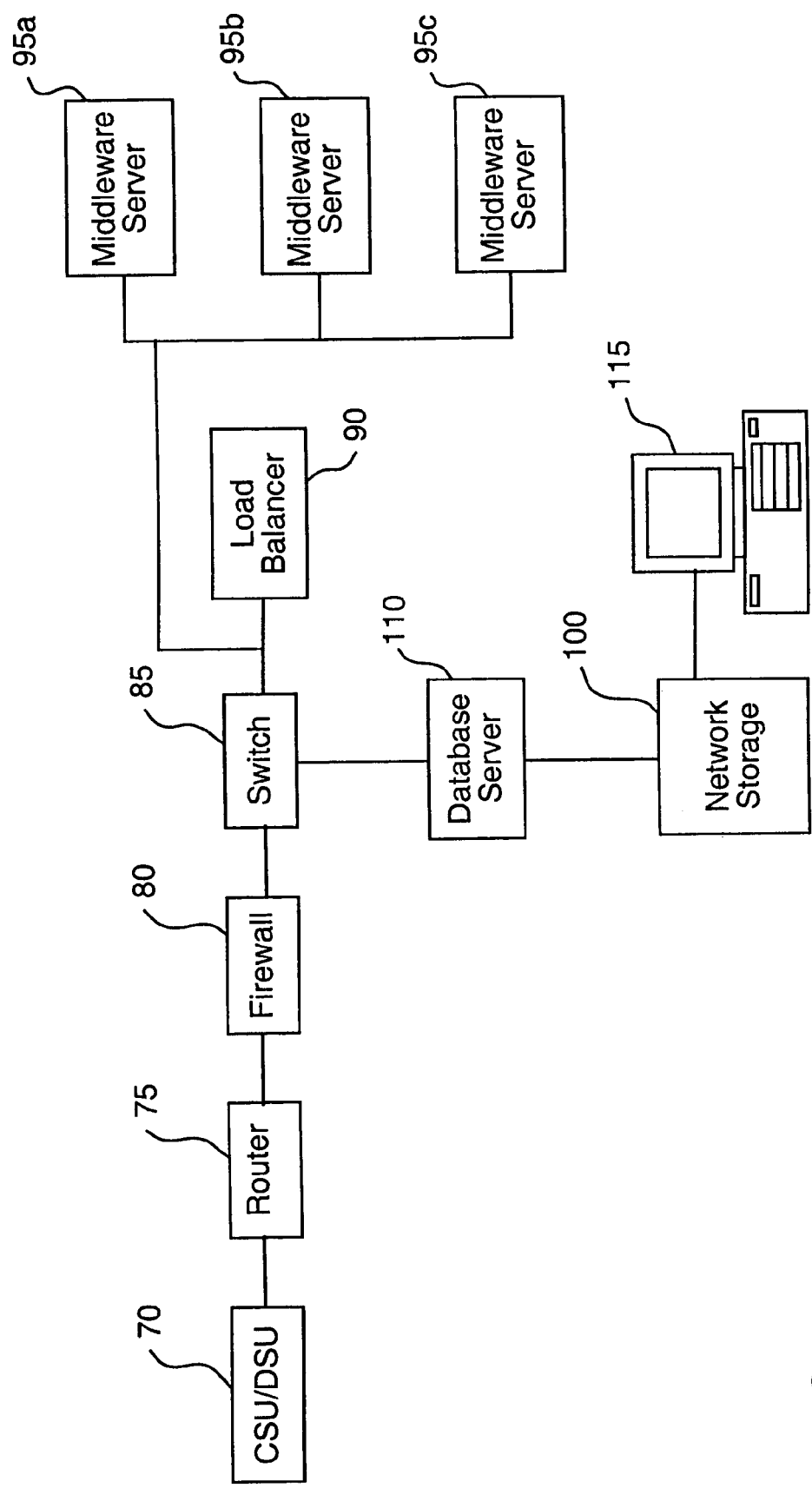
FIG. 3 is a block diagram of an embodiment of the central monitoring unit shown in FIG. 1.

Referring to FIG. 3, a block diagram of an embodiment of central monitoring unit 30 is shown. Central monitoring unit 30 includes CSU/DSU 70 which is connected to router 75, the main function of which is to take data requests or traffic, both incoming and outgoing, and direct such requests and traffic for processing or viewing on the web site maintained by central monitoring unit 30. Connected to router 75 is firewall 80. The main purpose of firewall 80 is to protect the remainder of central monitoring unit 30 from unauthorized or malicious intrusions. Switch 85, connected to firewall 80, is used to direct data flow between middleware servers 95a through 95c and database server 110. Load balancer 90 is provided to spread the workload of incoming requests among the identically configured middleware servers 95a through 95c. Load balancer 90, a suitable example of which is the F5 ServerIron product sold by Foundry Networks, Inc. of San Jose, Calif., analyzes the availability of each middleware server 95a through 95c, and the amount of system resources being used in each middleware server 95a through 95c, in order to spread tasks among them appropriately.

Central monitoring unit 30 includes network storage device 100, such as a storage area network or SAN, which acts as the central repository for data. In particular, network storage device 100 comprises a database that stores all data gathered for each individual user in the manners described above. An example of a suitable network storage device 100 is the Symmetrix product sold by EMC Corporation of Hopkinton, Mass. Although only one network storage device 100 is shown in FIG. 3, it will be understood that multiple network storage devices of various capacities could be used depending on the data storage needs of central monitoring unit 30. Central monitoring unit 30 also includes database server 110 which is coupled to network storage device 100. Database server 110 is made up of two main components: a large scale multiprocessor server and an enterprise type software server component such as the 8/8i component sold by Oracle Corporation of Redwood City, Calif., or the 506 7 component sold by Microsoft Corporation of Redmond, Wash. The primary functions of database server 110 are that of providing access upon request to the data stored in network storage device 100, and populating network storage device 100 with new data. Coupled to network storage device 100 is controller 115, which typically comprises a desktop personal computer, for managing the data stored in network storage device 100.

Middleware servers 95a through 95c, a suitable example of which is the 22OR Dual Processor sold by Sun Microsystems, Inc. of Palo Alto, Calif., each contain software for generating and maintaining the corporate or home web page or pages of the web site maintained by central monitoring unit 30. As is known in the art, a web page refers to a block or blocks of data available on the World-Wide Web comprising a file or files written in Hypertext Markup Language or HTML, and a web site commonly refers to any computer on the Internet running a World-Wide Web server process. The corporate or home web page or pages are the opening or landing web page or pages that are accessible by all members of the general public that visit the site by using the appropriate uniform resource locator or URL. As is known in the art, URLs are the form of address used on the World-Wide Web and provide a standard way of specifying the location of an object, typically a web page, on the Internet. Middleware servers 95a through 95c also each contain software for generating and maintaining the web pages of the web site of central monitoring unit 30 that can only be accessed by individuals that register and become members of central monitoring unit 30. The member users will be those individuals who wish to have their data stored at central monitoring unit 30. Access by such member users is controlled using passwords for security purposes. Preferred embodiments of those web pages are described in detail below and are generated using collected data that is stored in the database of network storage device 100.

Middleware servers 95a through 95c also contain software for requesting data from and writing data to network storage device 100 through database server 110. When an individual user desires to initiate a session with the central monitoring unit 30 for the purpose of entering data into the database of network storage device 100, viewing his or her data stored in the database of network storage device 100, or both, the user visits the home web page of central monitoring unit 30 using a browser program such as Internet Explorer distributed by Microsoft Corporation of Redmond, Wash., and logs in as a registered user. Load balancer 90 assigns the user to one of the middleware servers 95a through 95c, identified as the chosen middleware server. A user will preferably be assigned to a chosen middleware server for each entire session. The chosen middleware server authenticates the user using any one of many well known methods, to ensure that only the true user is permitted to access the information in the database. A member user may also grant access to his or her data to a third party such as a health care provider or a personal trainer. Each authorized third party may be given a separate password and may view the member user's data using a conventional browser. It is therefore possible for both the user and the third party to be the recipient of the data.

When the user is authenticated, the chosen middleware server requests, through database server 110, the individual user's data from network storage device 100 for a predetermined time period. The predetermined time period is preferably thirty days. The requested data, once received from network storage device 100, is temporarily stored by the chosen middleware server in cache memory. The cached data is used by the chosen middleware server as the basis for presenting information, in the form of web pages, to the user again through the user's browser. Each middleware server 95a through 95c is provided with appropriate software for generating such web pages, including software for manipulating and performing calculations utilizing the data to put the data in appropriate format for presentation to the user. Once the user ends his or her session, the data is discarded from cache. When the user initiates a new session, the process for obtaining and caching data for that user as described above is repeated. This caching system thus ideally requires that only one call to the network storage device 100 be made per session, thereby reducing the traffic that database server 110 must handle. Should a request from a user during a particular session require data that is outside of a predetermined time period of cached data already retrieved, a separate call to network storage device 100 may be performed by the chosen middleware server. The predetermined time period should be chosen, however, such that such additional calls are minimized. Cached data may also be saved in cache memory so that it can be reused when a user starts a new session, thus eliminating the need to initiate a new call to network storage device 100.

As described in connection with Table 2, the microprocessor of sensor device 10 may be programmed to derive information relating to an individual's physiological state based on the data indicative of one or more physiological parameters. Central monitoring unit 30, and preferably middleware servers 95a through 95c, may also be similarly programmed to derive such information based on the data indicative of one or more physiological parameters.

It is also contemplated that a user will input additional data during a session, for example, information relating to the user's eating or sleeping habits. This additional data is preferably stored by the chosen middleware server in a cache during the duration of the user's session. When the user ends the session, this additional new data stored in a cache is transferred by the chosen middleware server to database server 110 for population in network storage device 100. Alternatively, in addition to being stored in a cache for potential use during a session, the input data may also be immediately transferred to database server 110 for population in network storage device 100, as part of a write-through cache system which is well known in the art.

Data collected by sensor device 10 shown in FIG. 1 is periodically uploaded to central monitoring unit 30. Either by long distance wireless transmission or through personal computer 35, a connection to central monitoring unit 30 is made through an electronic network, preferably the Internet. In particular, connection is made to load balancer 90 through CSU/DSU 70, router 75, firewall 80 and switch 85. Load balancer 90 then chooses one of the middleware servers 95a through 95c to handle the upload of data, hereafter called the chosen middleware server. The chosen middleware server authenticates the user using any one of many well known methods. If authentication is successful, the data is uploaded to the chosen middleware server as described above, and is ultimately transferred to database server 110 for population in the network storage device 100.

Figure 4:
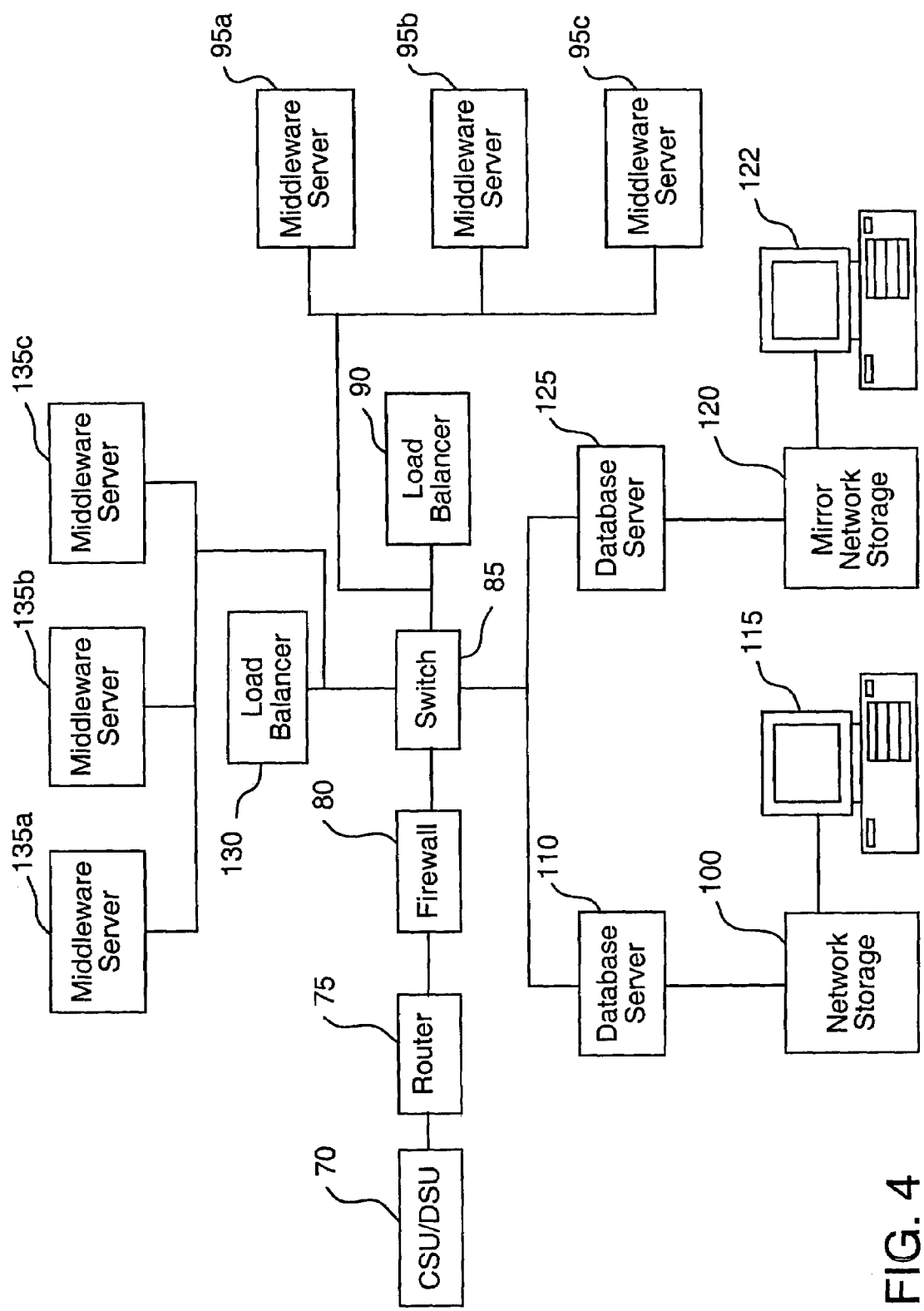
FIG. 4 is a block diagram of an alternate embodiment of the central monitoring unit shown in FIG. 1.

Referring to FIG. 4, an alternate embodiment of central monitoring unit 30 is shown. In addition to the elements shown and described with respect to FIG. 3, the embodiment of the central monitoring unit 30 shown in FIG. 4 includes a mirror network storage device 120 which is a redundant backup of network storage device 100. Coupled to mirror network storage device 120 is controller 122. Data from network storage device 100 is periodically copied to mirror network storage device 120 for data redundancy purposes.

Third parties such as insurance companies or research institutions may be given access, possibly for a fee, to certain of the information stored in mirror network storage device 120. Preferably, in order to maintain the confidentiality of the individual users who supply data to central monitoring unit 30, these third parties are not given access to such user's individual database records, but rather are only given access to the data stored in mirror network storage device 120 in aggregate form. Such third parties may be able to access the information stored in mirror network storage device 120 through the Internet using a conventional browser program. Requests from third parties may come in through CSU/DSU 70, router 75, firewall 80 and switch 85. In the embodiment shown in FIG. 4, a separate load balancer 130 is provided for spreading tasks relating to the accessing and presentation of data from mirror drive array 120 among identically configured middleware servers 135a through 135c. Middleware servers 135a through 135c each contain software for enabling the third parties to, using a browser, formulate queries for information from mirror network storage device 120 through separate database server 125. Middleware servers 135a through 135c also contain software for presenting the information obtained from mirror network storage device 120 to the third parties over the Internet in the form of web pages. In addition, the third parties can choose from a series of prepared reports that have information packaged along subject matter lines, such as various demographic categories.

As will be apparent to one of skill in the art, instead of giving these third parties access to the backup data stored in mirror network storage device 120, the third parties may be given access to the data stored in network storage device 100. Also, instead of providing load balancer 130 and middleware servers 135a through 135c, the same functionality, although at a sacrificed level of performance, could be provided by load balancer 90 and middleware servers 95a through 95c.

When an individual user first becomes a registered user or member, that user completes a detailed survey. The purposes of the survey are to: identify unique characteristics/circumstances for each user that they might need to address in order to maximize the likelihood that they will implement and maintain a healthy lifestyle as suggested by central monitoring unit 30; gather baseline data which will be used to set initial goals for the individual user and facilitate the calculation and display of certain graphical data output such as the Health Index pistons; identify unique user characteristics and circumstances that will help central monitoring unit 30 customize the type of content provided to the user in the Health Manager's Daily Dose; and identify unique user characteristics and circumstances that the Health Manager can guide the user to address as possible barriers to a healthy lifestyle through the problem-solving function of the Health Manager.

The specific information to be surveyed may include: key individual temperamental characteristics, including activity level, regularity of eating, sleeping, and bowel habits, initial response to situations, adaptability, persistence, threshold of responsiveness, intensity of reaction, and quality of mood; the user's level of independent functioning, i.e., self-organization and management, socialization, memory, and academic achievement skills; the user's ability to focus and sustain attention, including the user's level of arousal, cognitive tempo, ability to filter distractions, vigilance, and self-monitoring; the user's current health status including current weight, height, and blood pressure, most recent general physician visit, gynecological exam, and other applicable physician/healthcare contacts, current medications and supplements, allergies, and a review of current symptoms and/or health-related behaviors; the user's past health history, i.e., illnesses/surgeries, family history, and social stress events, such as divorce or loss of a job, that have required adjustment by the individual; the user's beliefs, values and opinions about health priorities, their ability to alter their behavior and, what might contribute to stress in their life, and how they manage it; the user's degree of self-awareness, empathy, empowerment, and self-esteem, and the user's current daily routines for eating, sleeping, exercise, relaxation and completing activities of daily living; and the user's perception of the temperamental characteristics of two key persons in their life, for example, their spouse, a friend, a co-worker, or their boss, and whether there are clashes present in their relationships that might interfere with a healthy lifestyle or contribute to stress.

Figure 5:
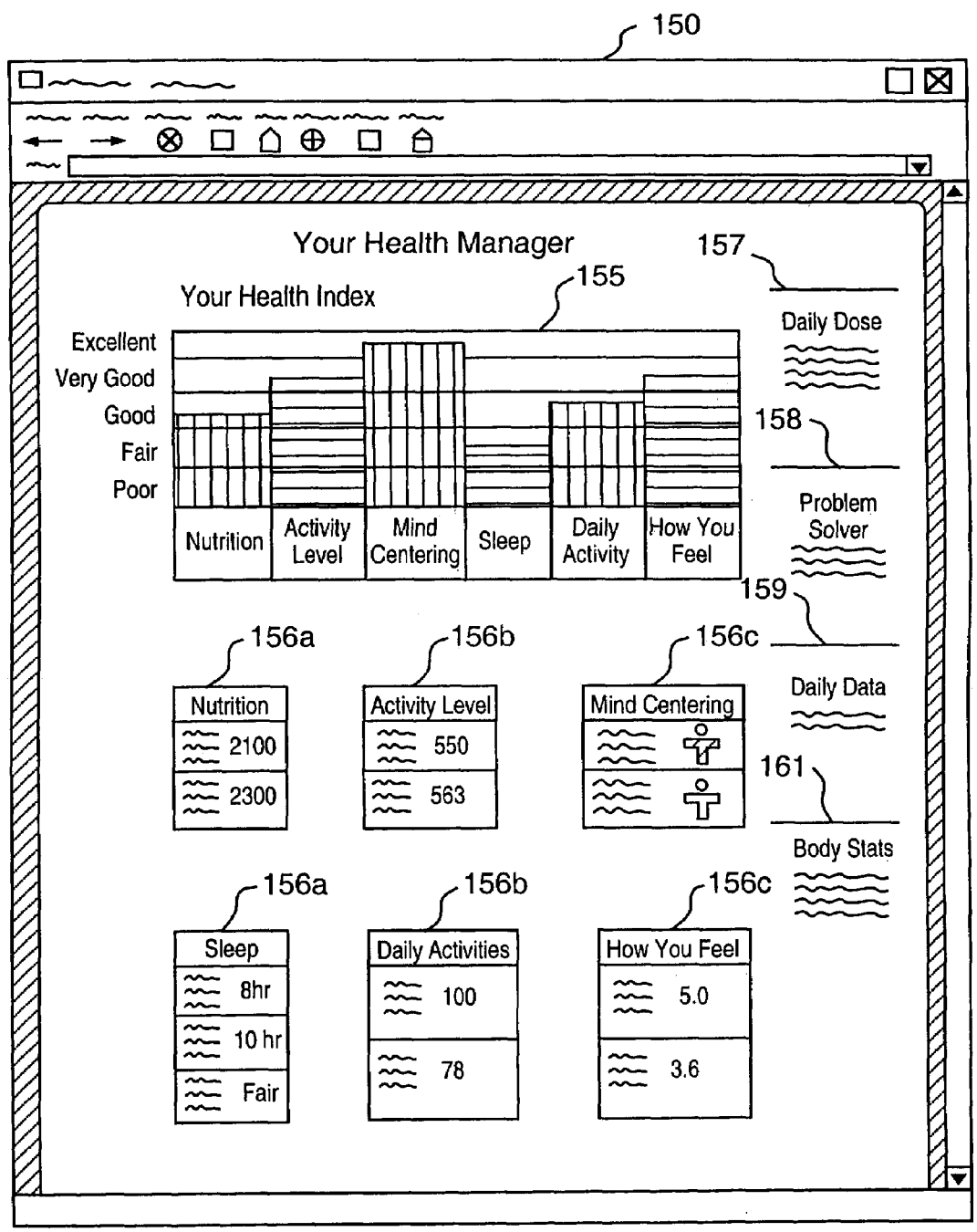
FIG. 5 is a representation of a preferred embodiment of the Health Manager web page according to an aspect of the present invention.

Each member user will have access, through the home web page of central monitoring unit 30, to a series of web pages customized for that user, referred to as the Health Manager. The opening Health Manager web page 150 is shown in FIG. 5. The Health Manager web pages are the main workspace area for the member user. The Health Manager web pages comprise a utility through which central monitoring unit 30 provides various types and forms of data, commonly referred to as analytical status data, to the user that is generated from the data it collects or generates, namely one or more of: the data indicative of various physiological parameters generated by sensor device 10; the data derived from the data indicative of various physiological parameters; the data indicative of various contextual parameters generated by sensor device 10; and the data input by the user. Analytical status data is characterized by the application of certain utilities or algorithms to convert one or more of the data indicative of various physiological parameters generated by sensor device 10, the data derived from the data indicative of various physiological parameters, the data indicative of various contextual parameters generated by sensor device 10, and the data input by the user into calculated health, wellness and lifestyle indicators. For example, based on data input by the user relating to the foods he or she has eaten, things such as calories and amounts of proteins, fats, carbohydrates, and certain vitamins can be calculated. As another example, skin temperature, heart rate, respiration rate, heat flow and/or GSR can be used to provide an indicator to the user of his or her stress level over a desired time period. As still another example, skin temperature, heat flow, beat-to-beat heart variability, heart rate, pulse rate, respiration rate, core temperature, galvanic skin response, EMG, EEG, EOG, blood pressure, oxygen consumption, ambient sound and body movement or motion as detected by a device such as an accelerometer can be used to provide indicators to the user of his or her sleep patterns over a desired time period.

Located on the opening Health Manager web page 150 is Health Index 155. Health Index 155 is a graphical utility used to measure and provide feedback to member users regarding their performance and the degree to which they have succeeded in reaching a healthy daily routine suggested by central monitoring unit 30. Health Index 155 thus provides an indication for the member user to track his or her progress. Health Index 155 includes six categories relating to the user's health and lifestyle: Nutrition, Activity Level, Mind Centering, Sleep, Daily Activities and How You Feel. The Nutrition category relates to what, when and how much a person eats and drinks. The Activity Level category relates to how much a person moves around. The Mind Centering category relates to the quality and quantity of time a person spends engaging in some activity that allows the body to achieve a state of profound relaxation while the mind becomes highly alert and focused. The Sleep category relates to the quality and quantity of a person's sleep. The Daily Activities category relates to the daily responsibilities and health risks people encounter. Finally, the How You Feel category relates to the general perception that a person has about how they feel on a particular day. Each category has an associated level indicator or piston that indicates, preferably on a scale ranging from poor to excellent, how the user is performing with respect to that category.

When each member user completes the initial survey described above, a profile is generated that provides the user with a summary of his or her relevant characteristics and life circumstances. A plan and/or set of goals is provided in the form of a suggested healthy daily routine. The suggested healthy daily routine may include any combination of specific suggestions for incorporating proper nutrition, exercise, mind centering, sleep, and selected activities of daily living in the user's life. Prototype schedules maybe offered as guides for how these suggested activities can be incorporated into the user's life. The user may periodically retake the survey, and based on the results, the items discussed above will be adjusted accordingly.

The Nutrition category is calculated from both data input by the user and sensed by sensor device 10. The data input by the user comprises the time and duration of breakfast, lunch, dinner and any snacks, and the foods eaten, the supplements such as vitamins that are taken, and the water and other liquids consumed during a relevant, pre-selected time period. Based upon this data and on stored data relating to known properties of various foods, central monitoring unit 30 calculates well known nutritional food values such as calories and amounts of proteins, fats, carbohydrates, vitamins, etc., consumed.

The Nutrition Health Index piston level is preferably determined with respect to the following suggested healthy daily routine: eat at least three meals; eat a varied diet consisting of 6-11 servings of bread, pasta, cereal, and rice, 2-4 servings fruit, 3-5 servings of vegetables, 2-3 servings of fish, meat, poultry, dry beans, eggs, and nuts, and 2-3 servings of milk, yogurt and cheese; and drink 8 or more 8 ounce glasses of water. This routine may be adjusted based on information about the user, such as sex, age, height and/or weight. Certain nutritional targets may also be set by the user or for the user, relating to daily calories, protein, fiber, fat, carbohydrates, and/or water consumption and percentages of total consumption. Parameters utilized in the calculation of the relevant piston level include the number of meals per day, the number of glasses of water, and the types and amounts of food eaten each day as input by the user.

Figure 6:
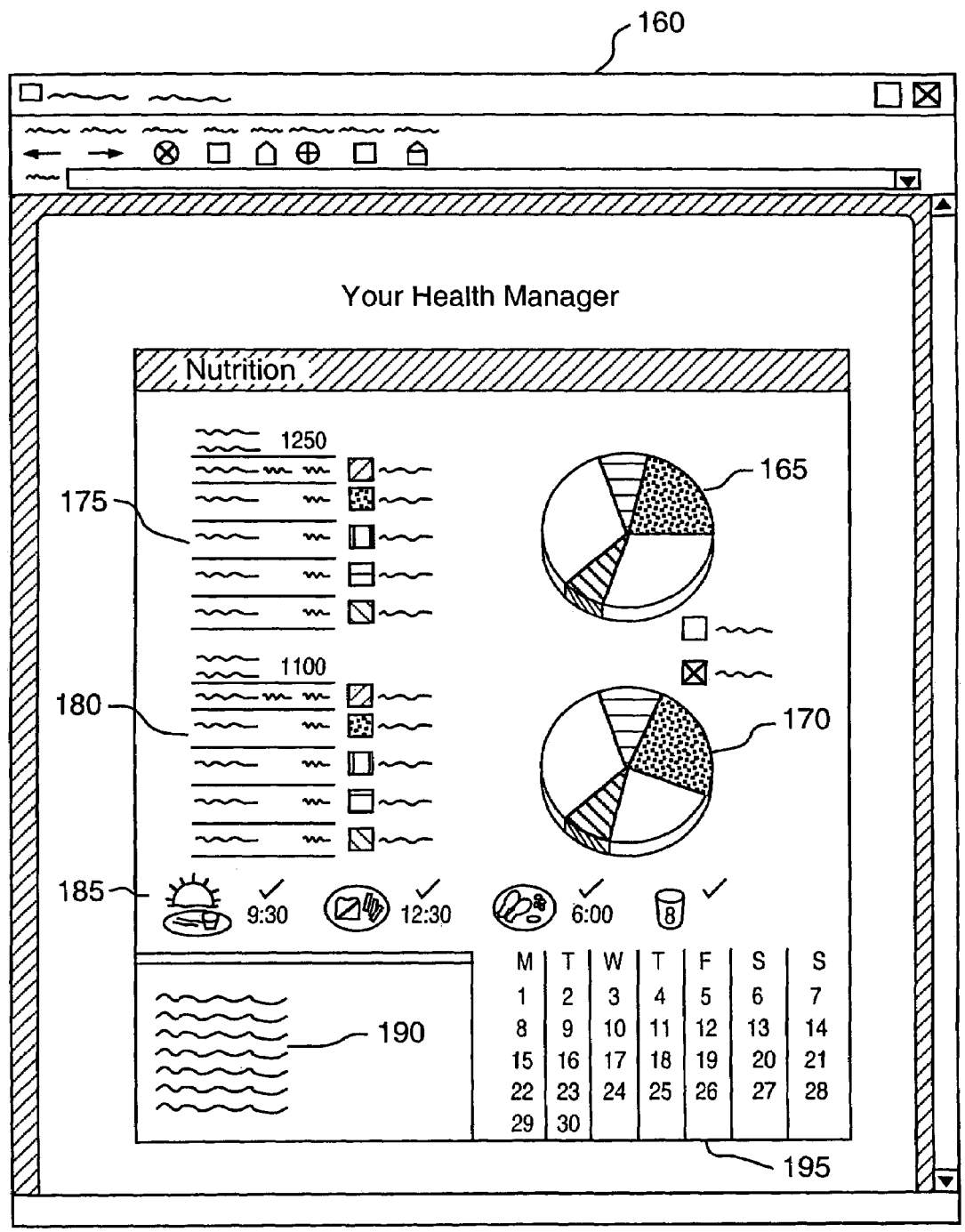
FIG. 6 is a representation of a preferred embodiment of the nutrition web page according to an aspect of the present invention.

Nutritional information is presented to the user through nutrition web page 160 as shown in FIG. 6. The preferred nutritional web page 160 includes nutritional fact charts 165 and 170 which illustrate actual and target nutritional facts, respectively as pie charts, and nutritional intake charts 175 and 180 which show total actual nutritional intake and target nutritional intake, respectively as pie charts. Nutritional fact charts 165 and 170 preferably show a percentage breakdown of items such as carbohydrates, protein and fat, and nutritional intake charts 175 and 180 are preferably broken down to show components such as total and target calories, fat, carbohydrates, protein, and vitamins. Web page 160 also includes meal and water consumption tracking 185 with time entries, hyperlinks 190 which allow the user to directly access nutrition-related news items and articles, suggestions for refining or improving daily routine with respect to nutrition and affiliate advertising elsewhere on the network, and calendar 195 for choosing between views having variable and selectable time periods. The items shown at 190 may be selected and customized based on information learned about the individual in the survey and on their performance as measured by the Health Index.

The Activity Level category of Health Index 155 is designed to help users monitor how and when they move around during the day and utilizes both data input by the user and data sensed by sensor device 10. The data input by the user may include details regarding the user's daily activities, for example the fact that the user worked at a desk from 8 a.m. to 5 p.m. and then took an aerobics class from 6 p.m. to 7 p.m. Relevant data sensed by sensor device 10 may include heart rate, movement as sensed by a device such as an accelerometer, heat flow, respiration rate, calories burned, GSR and hydration level, which may be derived by sensor device 60 or central monitoring unit 30. Calories burned maybe calculated in a variety of manners, including: the multiplication of the type of exercise input by the user by the duration of exercise input by the user; sensed motion multiplied by time of motion multiplied by a filter constant; or sensed heat flux multiplied by time multiplied by a filter constant.

The Activity Level Health Index piston level is preferably determined with respect to a suggested healthy daily routine that includes: exercising aerobically for a pre-set time period, preferably 20 minutes, or engaging in a vigorous lifestyle activity for a pre-set time period, preferably one hour, and burning at least a minimum target number of calories, preferably 205 calories, through the aerobic exercise and/or lifestyle activity. The minimum target number of calories may be set according to information about the user, such as sex, age, height and/or weight. Parameters utilized in the calculation of the relevant piston level include the amount of time spent exercising aerobically or engaging in a vigorous lifestyle activity as input by the user and/or sensed by sensor device 10, and the number of calories burned above pre-calculated energy expenditure parameters.

Figure 7:
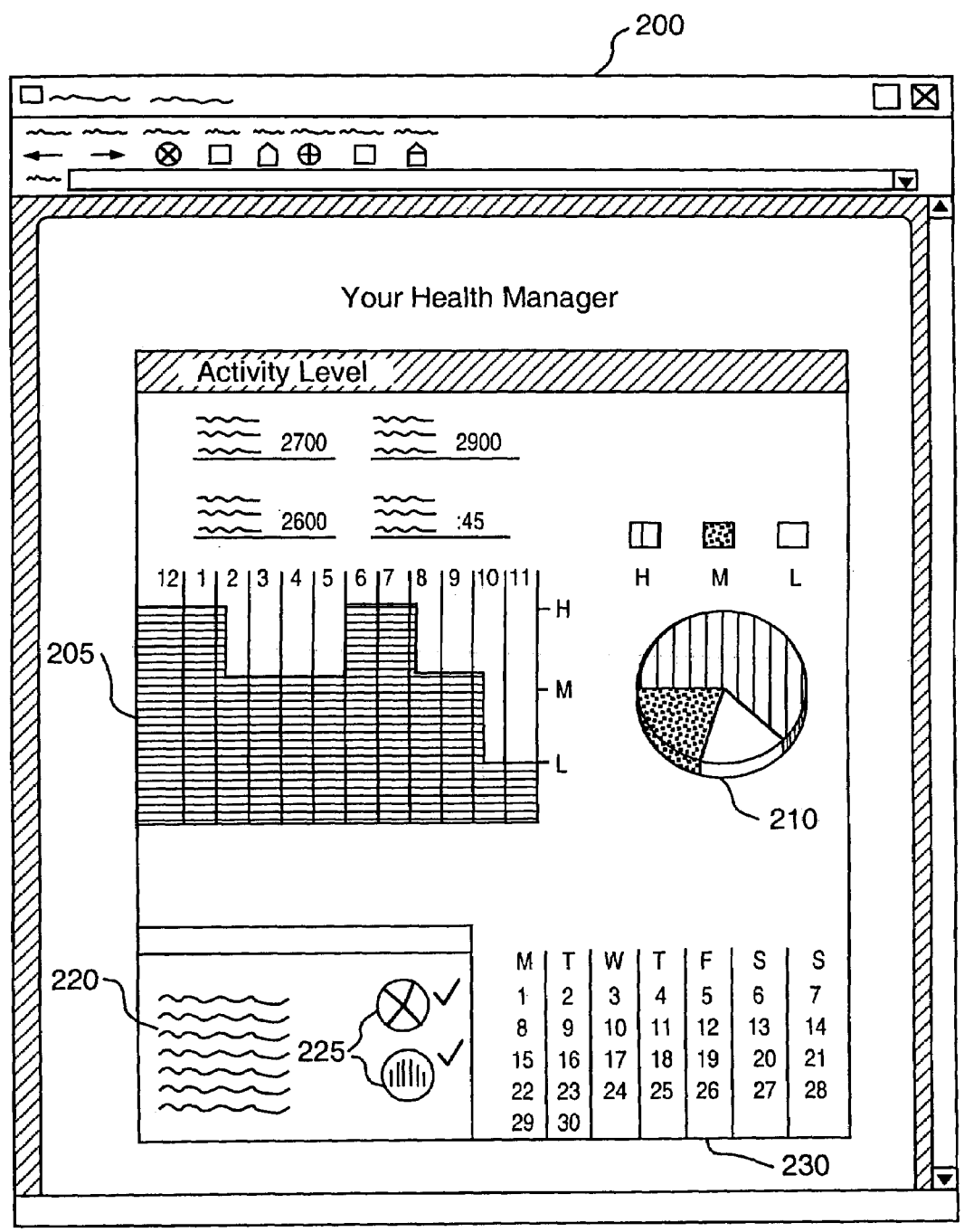
FIG. 7 is a representation of a preferred embodiment of the activity level web page according to an aspect of the present invention.

Information regarding the individual user's movement is presented to the user through activity level web page 200 shown in FIG. 7, which may include activity graph 205 in the form of a bar graph, for monitoring the individual user's activities in one of three categories: high, medium and low intensity with respect to a pre-selected unit of time. Activity percentage chart 210, in the form or a pie chart, may also be provided for showing the percentage of a pre-selected time period, such as one day, that the user spent in each category. Activity level web page 200 may also include calorie section 215 for displaying items such as total calories burned, daily target calories burned, total caloric intake, and duration of aerobic activity. Finally, activity level web page 200 may include at least one hyperlink 220 to allow a user to directly access relevant news items and articles, suggestions for refining or improving daily routine with respect to activity level and affiliate advertising elsewhere on the network. Activity level web page 200 may be viewed in a variety of formats, and may include user-selectable graphs and charts such as a bar graph, pie chart, or both, as selectable by Activity level check boxes 225. Activity level calendar 230 is provided for selecting among views having variable and selectable time periods. The items shown at 220 may be selected and customized based on information learned about the individual in the survey and on their performance as measured by the Health Index.

The Mind Centering category of Health Index 155 is designed to help users monitor the parameters relating to time spent engaging in certain activities which allow the body to achieve a state of profound relaxation while the mind becomes focused, and is based upon both data input by the user and data sensed by the sensor device 10. In particular, a user may input the beginning and end times of relaxation activities such as yoga or meditation. The quality of those activities as determined by the depth of a mind centering event can be measured by monitoring parameters including skin temperature, heart rate, respiration rate, and heat flow as sensed by sensor device 10. Percent change in GSR as derived either by sensor device 10 or central monitoring unit 30 may also be utilized.

The Mind Centering Health Index piston level is preferably calculated with respect to a suggested healthy daily routine that includes participating each day in an activity that allows the body to achieve profound relaxation while the mind stays highly focused for at least fifteen minutes. Parameters utilized in the calculation of the relevant piston level include the amount of time spent in a mind centering activity, and the percent change in skin temperature, heart rate, respiration rate, heat flow or GSR as sensed by sensor device 10 compared to a baseline which is an indication of the depth or quality of the mind centering activity.

Figure 8:
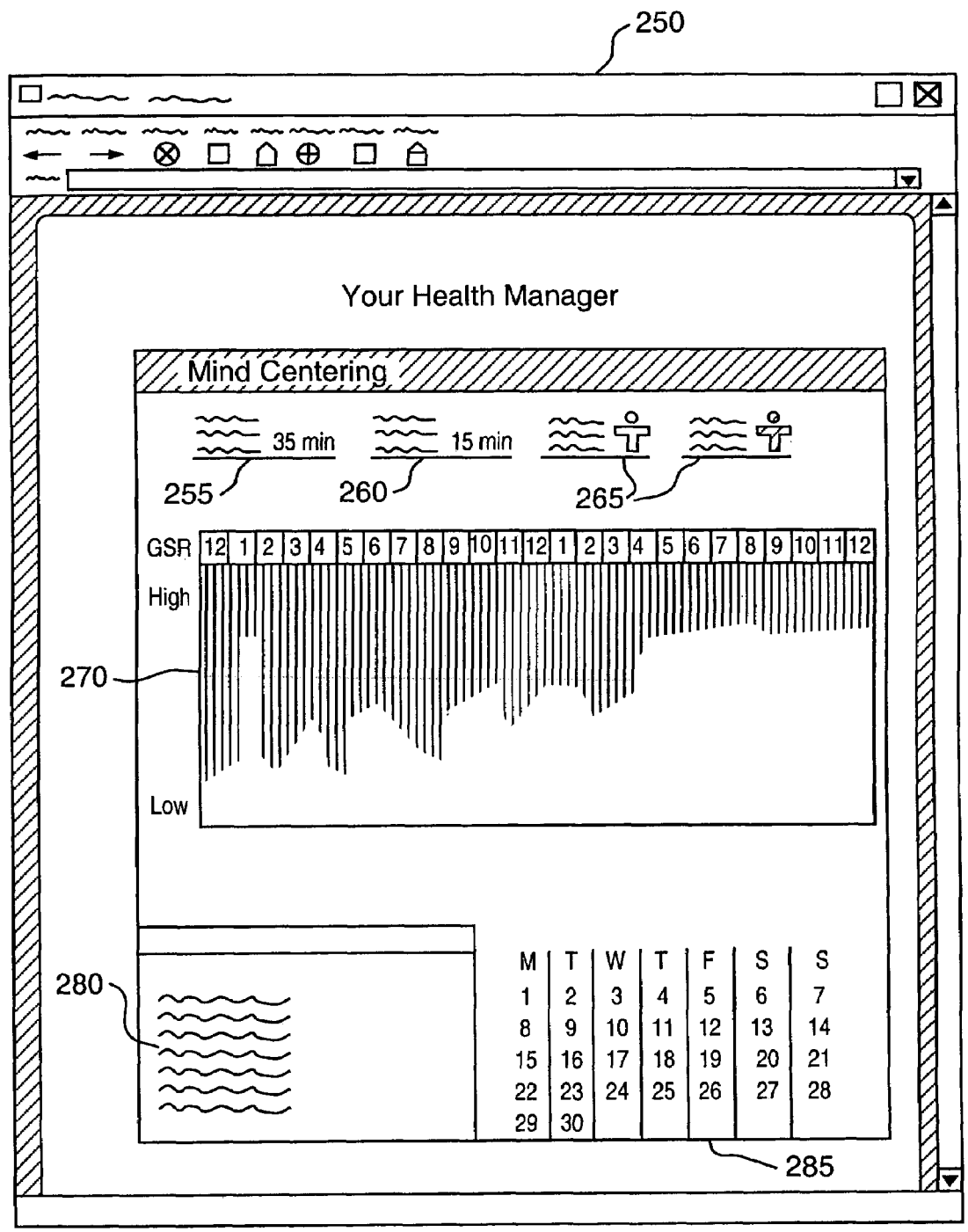
FIG. 8 is a representation of a preferred embodiment of the mind centering web page according to an aspect of the present invention.

Information regarding the time spent on self-reflection and relaxation is presented to the user through mind centering web page 250 shown in FIG. 8. For each mind centering activity, referred to as a session, the preferred mind centering web page 250 includes the time spent during the session, shown at 255, the target time, shown at 260, comparison section 265 showing target and actual depth of mind centering, or focus, and a histogram 270 that shows the overall level of stress derived from such things as skin temperature, heart rate, respiration rate, heat flow and/or GSR. In comparison section 265, the human figure outline showing target focus is solid, and the human figure outline showing actual focus ranges from fuzzy to solid depending on the level of focus. The preferred mind centering web page may also include an indication of the total time spent on mind centering activities, shown at 275, hyperlinks 280 which allow the user to directly access relevant news items and articles, suggestions for refining or improving daily routine with respect to mind centering and affiliate advertising, and a calendar 285 for choosing among views having variable and selectable time periods. The items shown at 280 may be selected and customized based on information learned about the individual in the survey and on their performance as measured by the Health Index.

The Sleep category of Health Index 155 is designed to help users monitor their sleep patterns and the quality of their sleep. It is intended to help users learn about the importance of sleep in their healthy lifestyle and the relationship of sleep to circadian rhythms, being the normal daily variations in body functions. The Sleep category is based upon both data input by the user and data sensed by sensor device 10. The data input by the user for each relevant time interval includes the times the user went to sleep and woke up and a rating of the quality of sleep. As noted in Table 2, the data from sensor device 10 that is relevant includes skin temperature, heat flow, beat-to-beat heart variability, heart rate, pulse rate, respiration rate, core temperature, galvanic skin response, EMG, EEG, EOG, blood pressure, and oxygen consumption. Also relevant is ambient sound and body movement or motion as detected by a device such as an accelerometer. This data can then be used to calculate or derive sleep onset and wake time, sleep interruptions, and the quality and depth of sleep.

The Sleep Health Index piston level is determined with respect to a healthy daily routine including getting a minimum amount, preferably eight hours, of sleep each night and having a predictable bed time and wake time. The specific parameters which determine the piston level calculation include the number of hours of sleep per night and the bed time and wake time as sensed by sensor device 10 or as input by the user, and the quality of the sleep as rated by the user or derived from other data.

Figure 9:
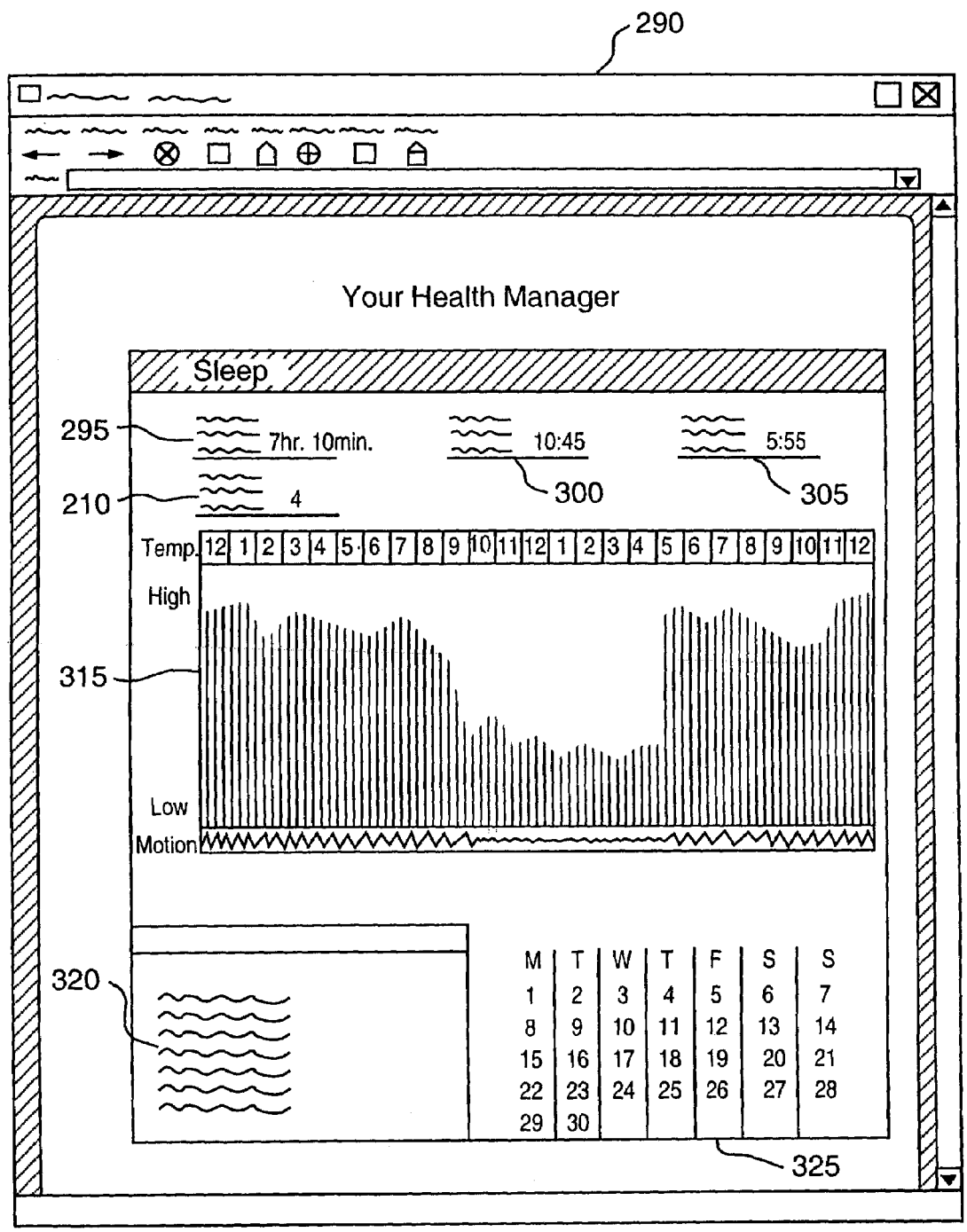
FIG. 9 is a representation of a preferred embodiment of the sleep web page according to an aspect of the present invention.

Information regarding sleep is presented to the user through sleep web page 290 shown in FIG. 9. Sleep web page 290 includes a sleep duration indicator 295, based on either data from sensor device 10 or on data input by the user, together with user sleep time indicator 300 and wake time indicator 305. A quality of sleep rating 310 input by the user may also be utilized and displayed. If more than a one day time interval is being displayed on sleep web page 290, then sleep duration indicator 295 is calculated and displayed as a cumulative value, and sleep time indicator 300, wake time indicator 305 and quality of sleep rating 310 are calculated and illustrated as averages. Sleep web page 290 also includes a user-selectable sleep graph 315 which calculates and displays one sleep related parameter over a pre-selected time interval. For illustrative purposes, FIG. 9 shows heat flow over a one-day period, which tends to be lower during sleeping hours and higher during waking hours. From this information, a person's bio-rhythms can be derived. Sleep graph 315 may also include a graphical representation of data from an accelerometer incorporated in sensor device 10 which monitors the movement of the body. The sleep web page 290 may also include hyperlinks 320 which allow the user to directly access sleep related news items and articles, suggestions for refining or improving daily routine with respect to sleep and affiliate advertising available elsewhere on the network, and a sleep calendar 325 for choosing a relevant time interval. The items shown at 320 maybe selected and customized based on information learned about the individual in the survey and on their performance as measured by the Health Index.

The Activities of Daily Living category of Health Index 155 is designed to help users monitor certain health and safety related activities and risks and is based entirely on data input by the user. The Activities of Daily Living category is divided into four sub-categories: personal hygiene, which allows the user to monitor activities such as brushing and flossing his or her teeth and showering; health maintenance, that tracks whether the user is taking prescribed medication or supplements and allows the user to monitor tobacco and alcohol consumption and automobile safety such as seat belt use; personal time, that allows the user to monitor time spent socially with family and friends, leisure, and mind centering activities; and responsibilities, that allows the user to monitor certain work and financial activities such as paying bills and household chores.

The Activities of Daily Living Health Index piston level is preferably determined with respect to the healthy daily routine described below. With respect to personal hygiene, the routine requires that the users shower or bathe each day, brush and floss teeth each day, and maintain regular bowel habits. With respect to health maintenance, the routine requires that the user take medications and vitamins and/or supplements, use a seat belt, refrain from smoking, drink moderately, and monitor health each day with the Health Manager. With respect to personal time, the routine requires the users to spend at least one hour of quality time each day with family and/or friends, restrict work time to a maximum of nine hours a day, spend some time on a leisure or play activity each day, and engage in a mind stimulating activity. With respect to responsibilities, the routine requires the users to do household chores, pay bills, be on time for work, and keep appointments. The piston level is calculated based on the degree to which the user completes a list of daily activities as determined by information input by the user.

Figure 10:
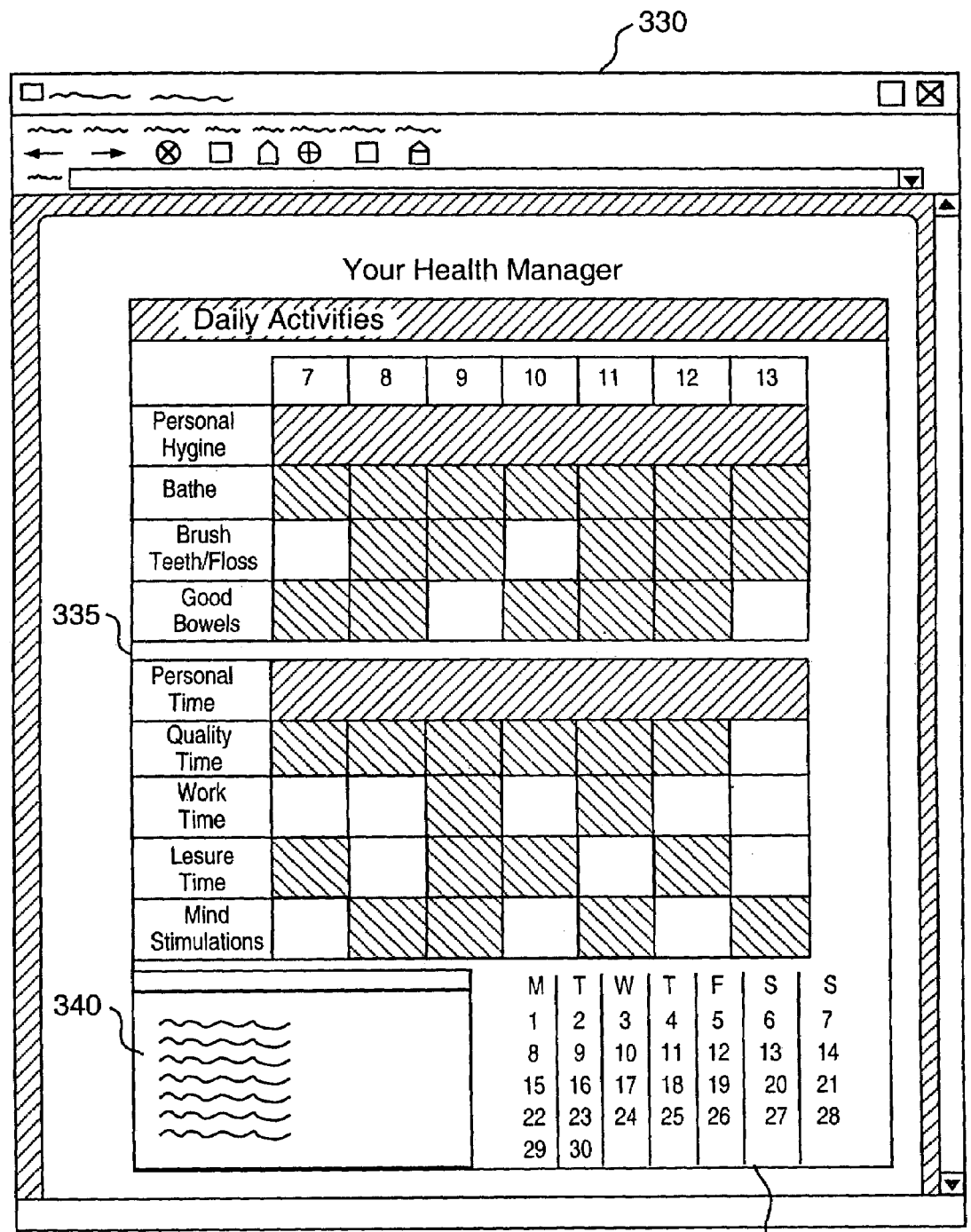
FIG. 10 is a representation of a preferred embodiment of the daily activities web page according to an aspect of the present invention.

Information relating to these activities is presented to the user through daily activities web page 330 shown in FIG. 10. In preferred daily activities web page 330, activities chart 335, selectable for one or more of the sub-categories, shows whether the user has done what is required by the daily routine. A colored or shaded box indicates that the user has done the required activity, and an empty, non-colored or shaded box indicates that the user has not done the activity. Activities chart 335 can be created and viewed in selectable time intervals. For illustrative purposes, FIG. 10 shows the personal hygiene and personal time sub-categories for a particular week. In addition, daily activities web page 330 may include daily activity hyperlinks 340 which allow the user to directly access relevant news items and articles, suggestions for improving or refining daily routine with respect to activities of daily living and affiliate advertising, and a daily activities calendar 345 for selecting a relevant time interval. The items shown at 340 may be selected and customized based on information learned about the individual in the survey and on their performance as measured by the Health Index.

The How You Feel category of Health Index 155 is designed to allow users to monitor their perception of how they felt on a particular day, and is based on information, essentially a subjective rating, that is input directly by the user. A user provides a rating, preferably on a scale of 1 to 5, with respect to the following nine subject areas: mental sharpness; emotional and psychological well being; energy level; ability to cope with life stresses; appearance; physical well being; self-control; motivation; and comfort in relating to others. Those ratings are averaged and used to calculate the relevant piston level.

Figure 11:
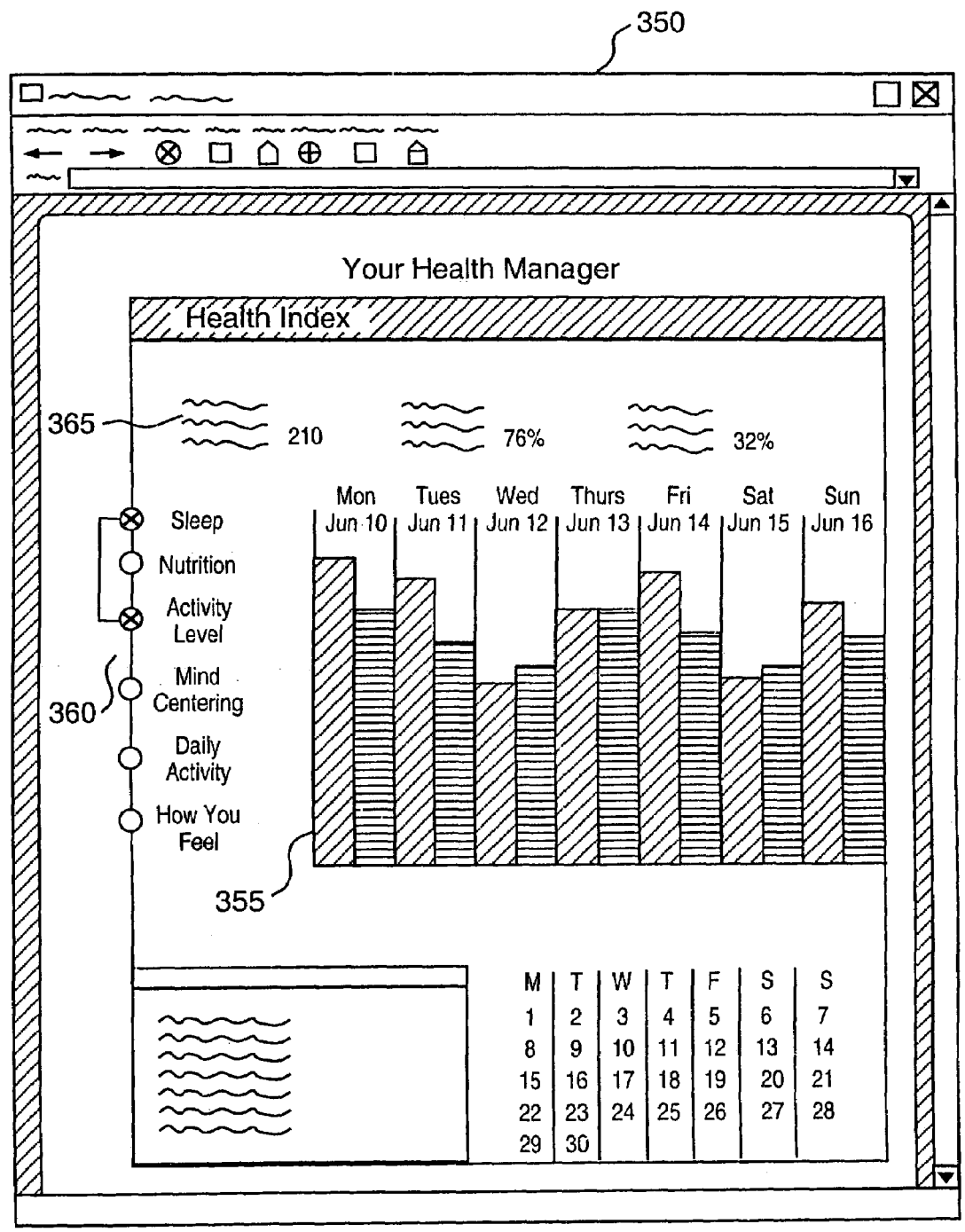
FIG. 11 is a representation of a preferred embodiment of the Health Index web page according to an aspect of the present invention.
Figure 12:
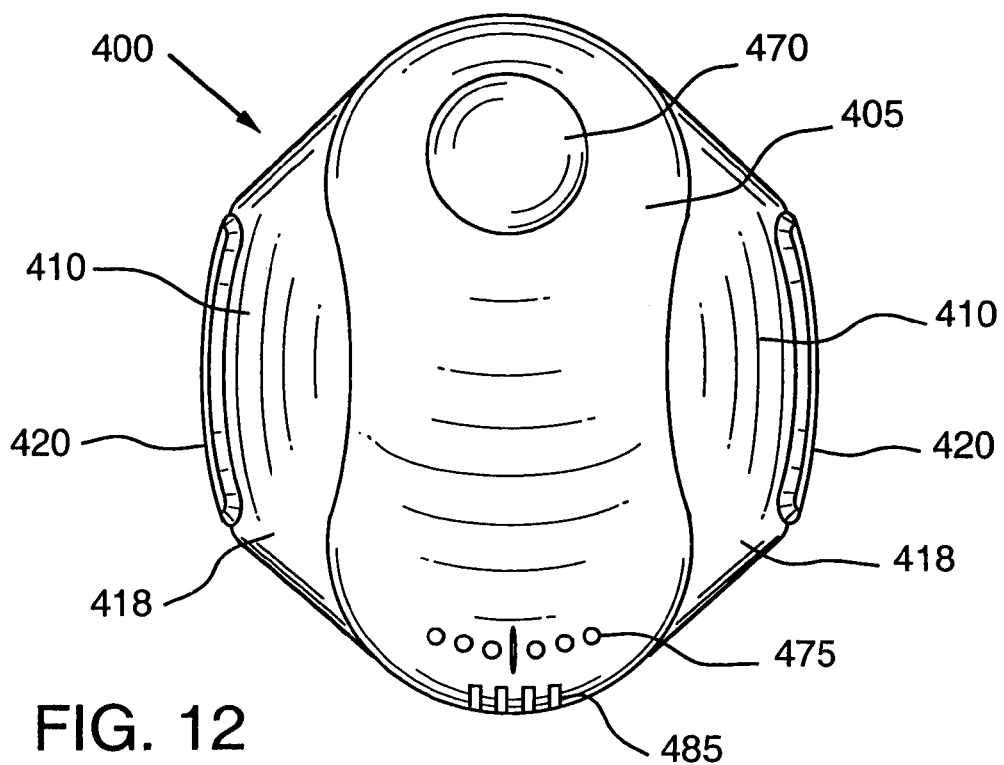
FIG. 12 is a front view of a specific embodiment of the sensor device shown in FIG. 1.

Referring to FIG. 11, Health Index web page 350 is shown. Health Index web page 350 enables users to view the performance of their Health Index over a user selectable time interval including any number of consecutive or non-consecutive days. Using Health Index selector buttons 360, the user can select to view the Health Index piston levels for one category, or can view a side-by-side comparison of the Health Index piston levels for two or more categories. For example, a user might want to just turn on Sleep to see if their overall sleep rating improved over the previous month, much in the same way they view the performance of their favorite stock. Alternatively, Sleep and Activity Level might be simultaneously displayed in order to compare and evaluate Sleep ratings with corresponding Activity Level ratings to determine if any day-to-day correlations exist. Nutrition ratings might be displayed with How You Feel for a pre-selected time interval to determine if any correlation exists between daily eating habits and how they felt during that interval. For illustrative purposes, FIG. 11 illustrates a comparison of Sleep and Activity Level piston levels for the week of June 10 through June 16. Health Index web page 350 also includes tracking calculator 365 that displays access information and statistics such as the total number of days the user has logged in and used the Health Manager, the percentage of days the user has used the Health Manager since becoming a subscriber, and percentage of time the user has used the sensor device 10 to gather data.

Referring again to FIG. 5, opening Health Manager web page 150 may include a plurality of user selectable category summaries 156a through 156f, one corresponding to each of the Health Index 155 categories. Each category summary 156a through 156f presents a pre-selected filtered subset of the data associated with the corresponding category. Nutrition category summary 156a displays daily target and actual caloric intake. Activity Level category summary 156b displays daily target and actual calories burned. Mind Centering category summary 156c displays target and actual depth of mind centering or focus. Sleep category summary 156d displays target sleep, actual sleep, and a sleep quality rating. Daily Activities category summary 156e displays a target and actual score based on the percentage of suggested daily activities that are completed. The How You Feel category summary 156f shows a target and actual rating for the day.

Opening Health Manager web page 150 also may include Daily Dose section 157 which provides, on a daily time interval basis, information to the user, including, but not limited to, hyperlinks to news items and articles, commentary and reminders to the user based on tendencies, such as poor nutritional habits, determined from the initial survey. The commentary for Daily Dose 157 may, for example, be a factual statement that drinking 8 glasses of water a day can reduce the risk of colon cancer by as much as 32%, accompanied by a suggestion to keep a cup of water by your computer or on your desk at work and refill often. Opening Health Manager web page 150 also may include a Problem Solver section 158 that actively evaluates the user's performance in each of the categories of Health Index 155 and presents suggestions for improvement. For example, if the system detects that a user's Sleep levels have been low, which suggest that the user has been having trouble sleeping, Problem Solver 158 can provide suggestions for way to improve sleep. Problem Solver 158 also may include the capability of user questions regarding improvements in performance. Opening Health Manager web page 150 may also include a Daily Data section 159 that launches an input dialog box. The input dialog box facilitates input by the user of the various data required by the Health Manager. As is known in the art, data entry may be in the form of selection from pre-defined lists or general free form text input. Finally, opening Health Manager web page 150 may include Body Stats section 161 which may provide information regarding the user's height, weight, body measurements, body mass index or BMI, and vital signs such as heart rate, blood pressure or any of the identified physiological parameters.

Figure 17:
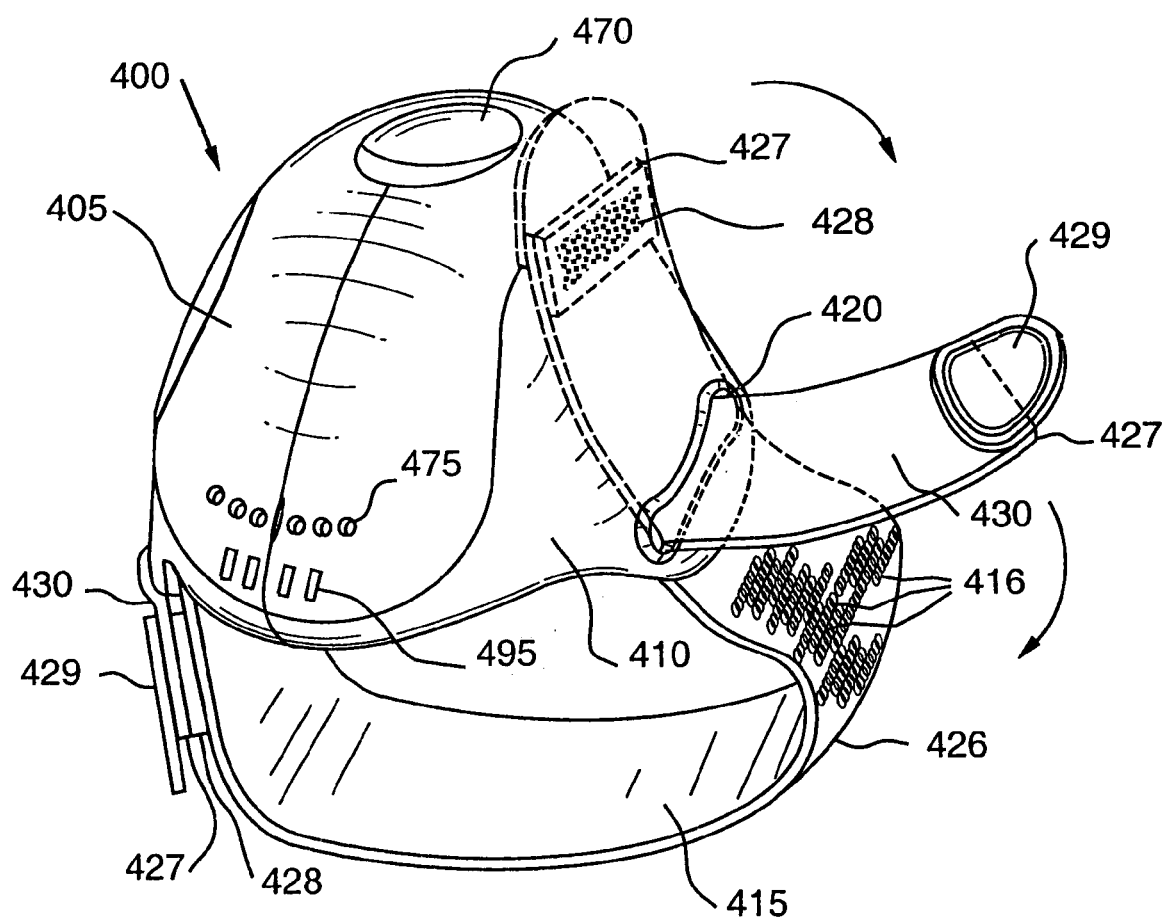

Referring to FIGS. 12-17, a specific embodiment of sensor device 10 is shown which is in the form of an armband adapted to be worn by an individual on his or her upper arm, between the shoulder and the elbow. The specific embodiment of sensor device 10 shown in FIGS. 12-17 will, for convenience, be referred to as armband sensor device 400. Armband sensor device 400 includes computer housing 405, flexible wing body 410, and, as shown in FIG. 17, elastic strap 415. Computer housing 405 and flexible wing body 410 are preferably made of a flexible urethane material or an elastomeric material such as rubber or a rubber-silicone blend by a molding process. Flexible wing body 410 includes first and second wings 418 each having a thru-hole 420 located near the ends 425 thereof. First and second wings 418 are adapted to wrap around a portion of the wearer's upper arm.

Elastic strap 415 is used to removably affix armband sensor device 400 to the individual's upper arm. As seen in FIG. 17, bottom surface 426 of elastic strap 415 is provided with velcro loops 416 along a portion thereof. Each end 427 of elastic strap 415 is provided with velcro book patch 428 on bottom surface 426 and pull tab 429 on top surface 430. A portion of each pull tab 429 extends beyond the edge of each end 427.

In order to wear armband sensor device 400, a user inserts each end 427 of elastic strap 415 into a respective thru-hole 420 of flexible wing body 410. The user then places his arm through the loop created by elastic strap 415, flexible wing body 410 and computer housing 405. By pulling each pull tab 429 and engaging velcro hook patches 428 with velcro loops 416 at a desired position along bottom surface 426 of elastic strap 415, the user can adjust elastic strap 415 to fit comfortably. Since velcro hook patches 428 can be engaged with velcro loops 416 at almost any position along bottom surface 426, armband sensor device 400 can be adjusted to fit arms of various sizes. Also, elastic strap 415 may be provided in various lengths to accommodate a wider range of arm sizes. As will be apparent to one of skill in the art, other means of fastening and adjusting the size of elastic strap may be used, including, but not limited to, snaps, buttons, or buckles. It is also possible to use two elastic straps that fasten by one of several conventional means including velcro, snaps, buttons, buckles or the like, or merely a single elastic strap affixed to wings 418.

Alternatively, instead of providing thru-holes 420 in wings 418, loops having the shape of the letter D, not shown, may be attached to ends 425 of wings 418 by one of several conventional means. For example, a pin, not shown, may be inserted through ends 425, wherein the pin engages each end of each loop. In this configuration, the D-shaped loops would serve as connecting points for elastic strap 415, effectively creating a thru-hole between each end 425 of each wing 418 and each loop.

Figure 18:
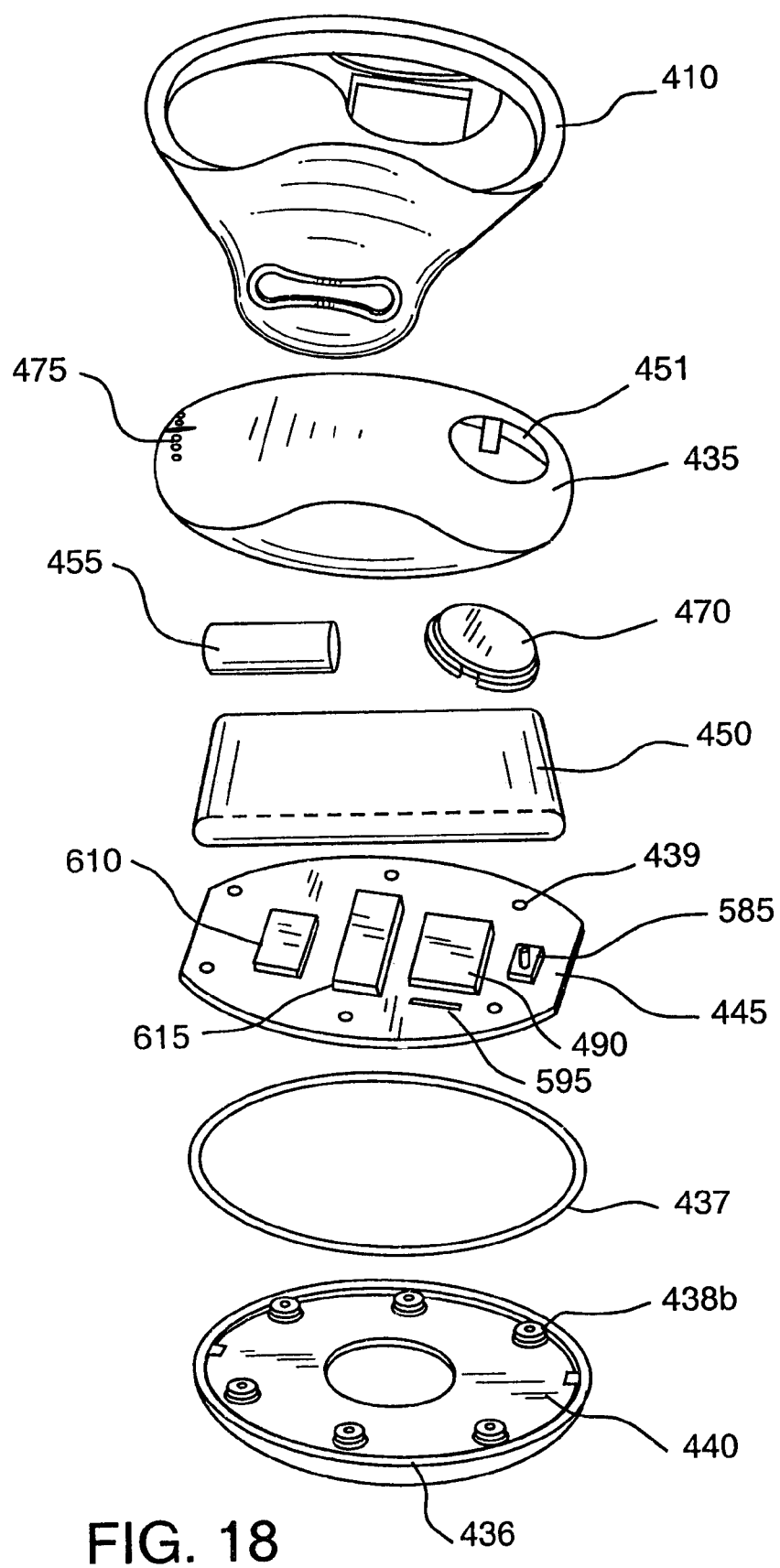
FIG. 18 is an exploded side perspective view of a specific embodiment of the sensor device shown in FIG. 1.

As shown in FIG. 18, which is an exploded view of armband sensor device 400, computer housing 405 includes a top portion 435 and a bottom portion 440. Contained within computer housing 405 are printed circuit board or PCB 445, rechargeable battery 450, preferably a lithium ion battery, and vibrating motor 455 for providing tactile feedback to the wearer, such as those used in pagers, suitable examples of which are the Model 12342 and 12343 motors sold by MG Motors Ltd. of the United Kingdom.

Top portion 435 and bottom portion 440 of computer housing 405 sealingly mate along groove 436 into which O-ring 437 is fit, and may be affixed to one another by screws, not shown, which pass through screw holes 438a and stiffeners 438b of bottom portion 440 and apertures 439 in PCB 445 and into threaded receiving stiffeners 451 of top portion 435. Alternately, top portion 435 and bottom portion 440 may be snap fit together or affixed to one another with an adhesive. Preferably, the assembled computer housing 405 is sufficiently water resistant to permit armband sensor device 400 to be worn while swimming without adversely affecting the performance thereof.

Figure 13:
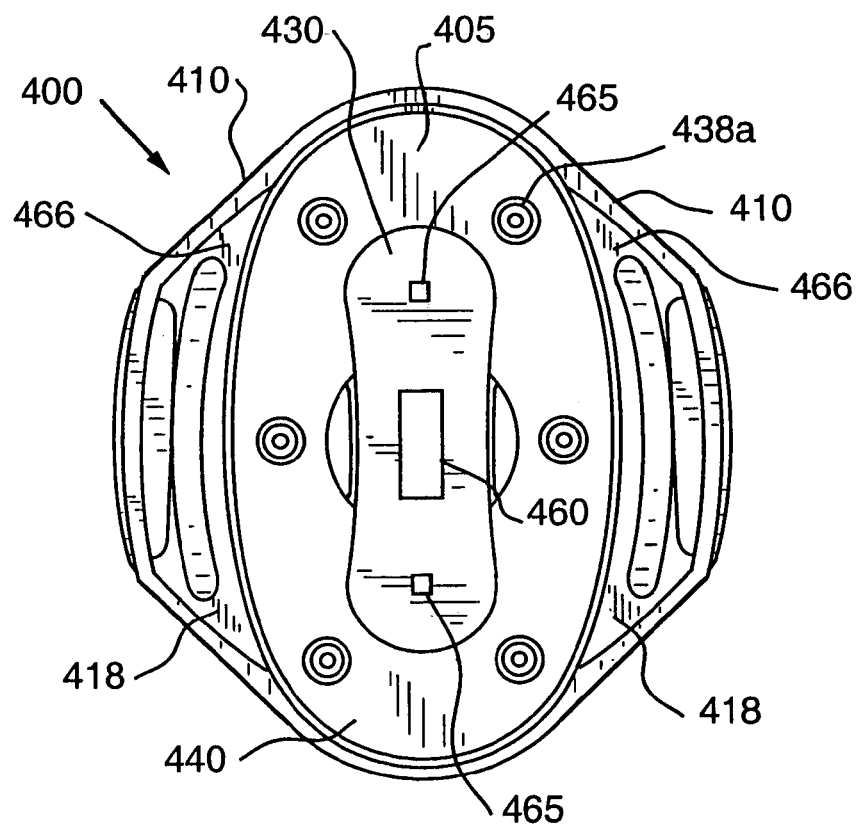
FIG. 13 is a back view of a specific embodiment of the sensor device shown in FIG. 1.
Figure 14:
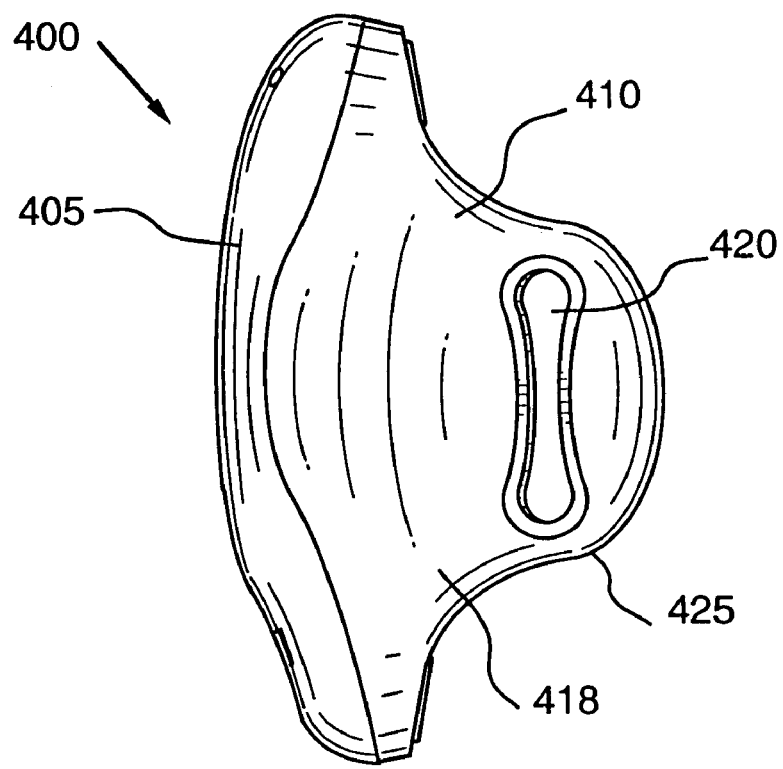
FIG. 14 is a side view of a specific embodiment of the sensor device shown in FIG. 1.
Figure 15:
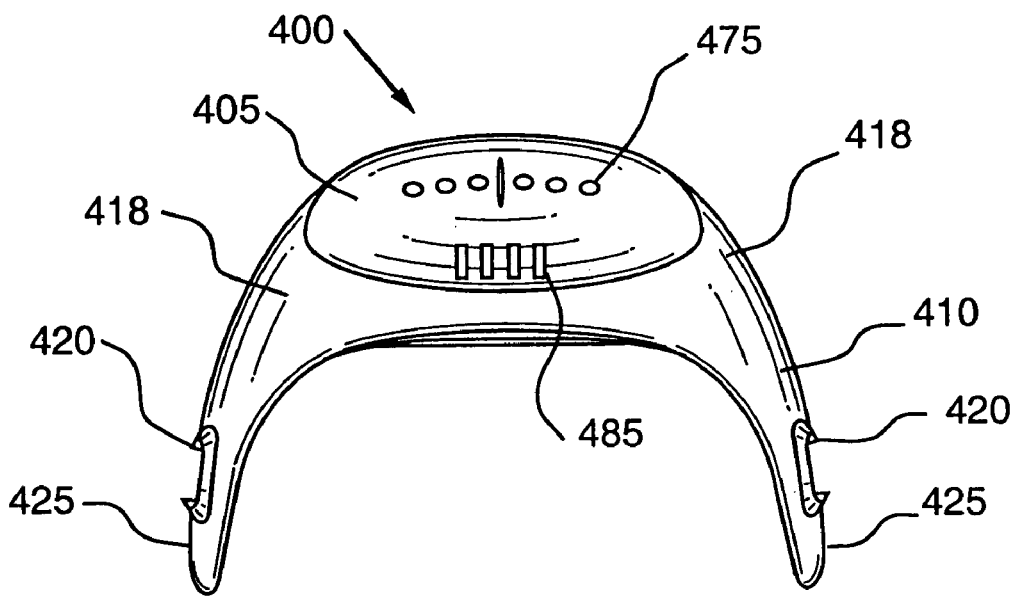
FIG. 15 is a bottom view of a specific embodiment of the sensor device shown in FIG. 1.
Figure 16:
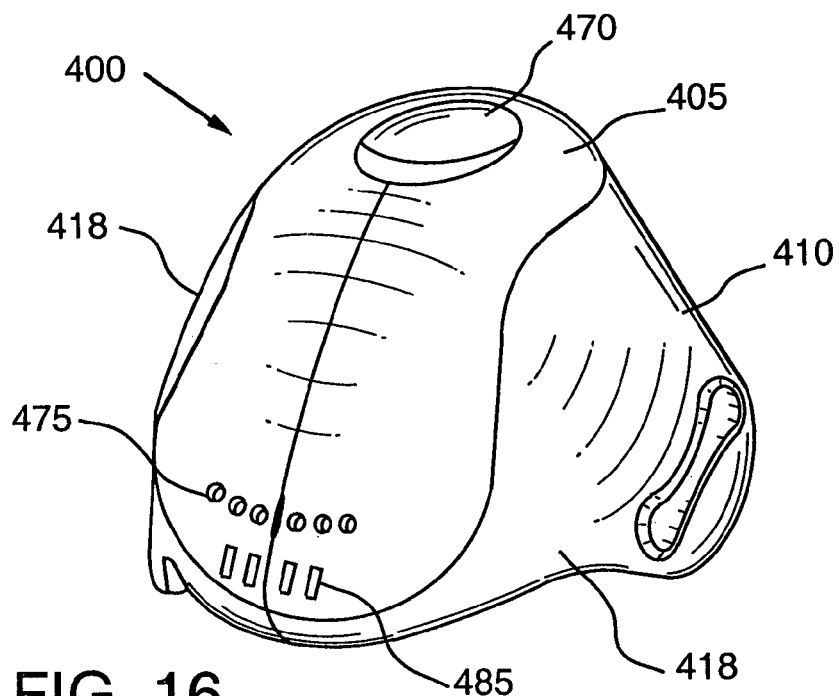
FIGS. 16 and 17 are front perspective views of a specific embodiment of the sensor device shown in FIG. 1.

As can be seen in FIG. 13, bottom portion 440 includes, on a bottom side thereof, a raised platform 430. Affixed to raised platform 430 is heat flow or flux sensor 460, a suitable example of which is the micro-foil heat flux sensor sold by RdF Corporation of Hudson, N.H. Heat flux sensor 460 functions as a self-generating thermopile transducer, and preferably includes a carrier made of a polyamide film. Bottom portion 440 may include on a top side thereof, that is on a side opposite the side to which heat flux sensor 460 is affixed, a heat sink, not shown, made of a suitable metallic material such as aluminum. Also affixed to raised platform 430 are GSR sensors 465, preferably comprising electrodes formed of a material such as conductive carbonized rubber, gold or stainless steel. Although two GSR sensors 465 are shown in FIG. 13, it will be appreciated by one of skill in the art that the number of GSR sensors 465 and the placement thereof on raised platform 430 can vary as long as the individual GSR sensors 465, i.e., the electrodes, are electrically isolated from one another. By being affixed to raised platform 430, heat flux sensor 460 and GSR sensors 465 are adapted to be in contact with the wearer's skin when armband sensor device 400 is worn. Bottom portion 440 of computer housing 405 may also be provided with a removable and replaceable soft foam fabric pad, not shown, on a portion of the surface thereof that does not include raised platform 430 and screw holes 438a. The soft foam fabric is intended to contact the wearer's skin and make armband sensor device 400 more comfortable to wear.

Electrical coupling between heat flux sensor 460, GSR sensors 465, and PCB 445 may be accomplished in one of various known methods. For example, suitable wiring, not shown, may be molded into bottom portion 440 of computer housing 405 and then electrically connected, such as by soldering, to appropriate input locations on PCB 445 and to heat flux sensor 460 and GSR sensors 465. Alternatively, rather than molding wiring into bottom portion 440, thru-holes may be provided in bottom portion 440 through which appropriate wiring may pass. The thru-holes would preferably be provided with a water tight seal to maintain the integrity of computer housing 405.

Rather than being affixed to raised platform 430 as shown in FIG. 13, one or both of heat flux sensor 460 and GSR sensors 465 may be affixed to the inner portion 466 of flexible wing body 410 on either or both of wings 418 so as to be in contact with the wearer's skin when armband sensor device 400 is worn. In such a configuration, electrical coupling between heat flux sensor 460 and GSR sensors 465, whichever the case may be, and the PCB 445 may be accomplished through suitable wiring, not shown, molded into flexible wing body 410 that passes through one or more thru-holes in computer housing 405 and that is electrically connected, such as by soldering, to appropriate input locations on PCB 445. Again, the thru-holes would preferably be provided with a water tight seal to maintain the integrity of computer housing 405. Alternatively, rather than providing thru-holes in computer housing 405 through which the wiring passes, the wiring may be captured in computer housing 405 during an overmolding process, described below, and ultimately soldered to appropriate input locations on PCB 445.

As shown in FIGS. 12, 16, 17 and 18, computer housing 405 includes a button 470 that is coupled to and adapted to activate a momentary switch 585 on PCB 445. Button 470 may be used to activate armband sensor device 400 for use, to mark the time an event occurred or to request system status information such as battery level and memory capacity. When button 470 is depressed, momentary switch 585 closes a circuit and a signal is sent to processing unit 490 on PCB 445. Depending on the time interval for which button 470 is depressed, the generated signal triggers one of the events just described. Computer housing 405 also includes LEDs 475, which may be used to indicate battery level or memory capacity or to provide visual feedback to the wearer. Rather than LEDs 475, computer housing 405 may also include a liquid crystal display or LCD to provide battery level, memory capacity or visual feedback information to the wearer. Battery level, memory capacity or feedback information may also be given to the user tactily or audibly.

Armband sensor device 400 may be adapted to be activated for use, that is collecting data, when either of GSR sensors 465 or heat flux sensor 460 senses a particular condition that indicates that armband sensor device 400 has been placed in contact with the user's skin. Also, armband sensor device 400 may be adapted to be activated for use when one or more of heat flux sensor 460, GSR sensors 465, accelerometer 495 or 550, or any other device in communication with armband sensor device 400, alone or in combination, sense a particular condition or conditions that indicate that the armband sensor device 400 has been placed in contact with the user's skin for use. At other times, armband sensor device 400 would be deactivated, thus preserving battery power.

Figure 19:
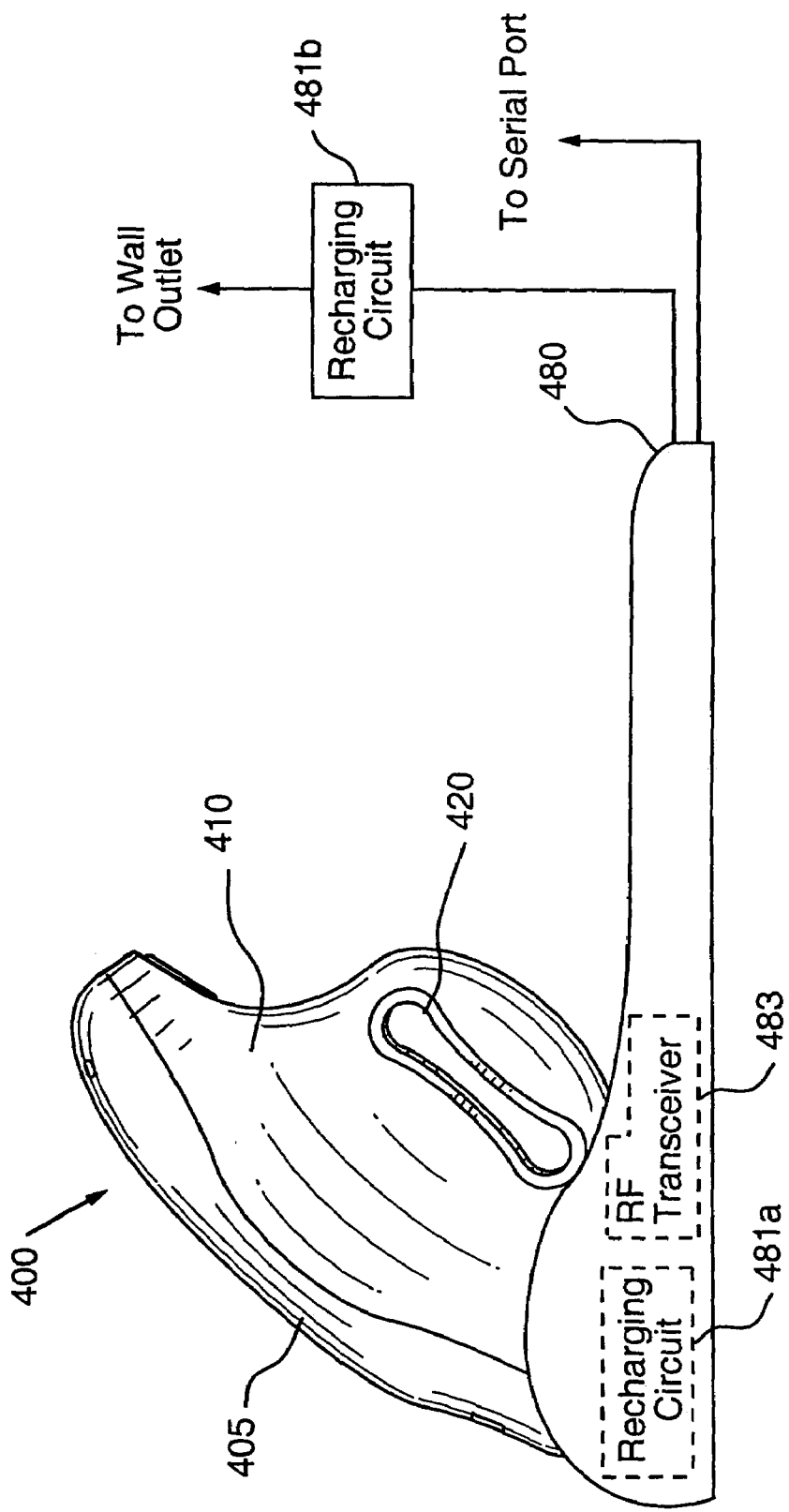
FIG. 19 is a side view of the sensor device shown in FIGS. 12 through 18 inserted into a battery recharger unit.

Computer housing 405 is adapted to be coupled to a battery recharger unit 480 shown in FIG. 19 for the purpose of recharging rechargeable battery 450. Computer housing 405 includes recharger contacts 485, shown in FIGS. 12, 15, 16 and 17, that are coupled to rechargeable battery 450. Recharger contacts 485 may be made of a material such as brass, gold or stainless steel, and are adapted to mate with and be electrically coupled to electrical contacts, not shown, provided in battery recharger unit 480 when armband sensor device 400 is placed therein. The electrical contacts provided in battery recharger unit 480 may be coupled to recharging circuit 481a provided inside battery recharger unit 480. In this configuration, recharging circuit 481 would be coupled to a wall outlet, such as by way of wiring including a suitable plug that is attached or is attachable to battery recharger unit 480. Alternatively, electrical contacts 480 may be coupled to wiring that is attached to or is attachable to battery recharger unit 480 that in turn is coupled to recharging circuit 481b external to battery recharger unit 480. The wiring in this configuration would also include a plug, not shown, adapted to be plugged into a conventional wall outlet.

Figure 20:
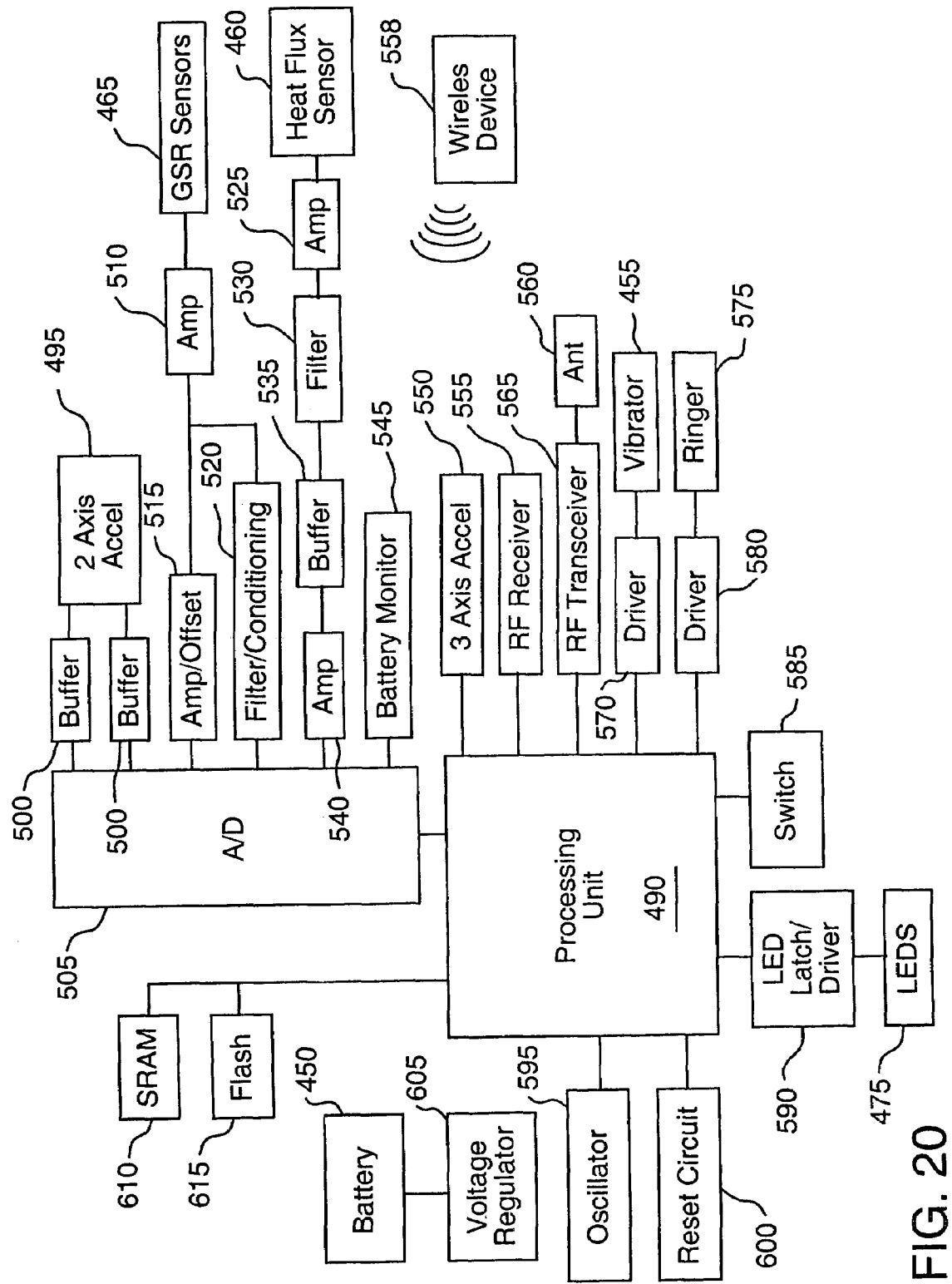
FIG. 20 is a block diagram illustrating all of the components either mounted on or coupled to the printed circuit board forming a part of the sensor device shown in FIGS. 12 through 18.

Also provided inside battery recharger unit 480 is RF transceiver 483 adapted to receive signals from and transmit signals to RF transceiver 565 provided in computer housing 405 and shown in FIG. 20. RF transceiver 483 is adapted to be coupled, for example by a suitable cable, to a serial port, such as an RS 232 port or a USB port, of a device such as personal computer 35 shown in FIG. 1. Thus, data may be uploaded from and downloaded to armband sensor device 400 using RF transceiver 483 and RF transceiver 565. It will be appreciated that although RF transceivers 483 and 565 are shown in FIGS. 19 and 20, other forms of wireless transceivers may be used, such as infrared transceivers. Alternatively, computer housing 405 may be provided with additional electrical contacts, not shown, that would be adapted to mate with and be electrically coupled to additional electrical contacts, not shown, provided in battery recharger unit 480 when armband sensor device 400 is placed therein. The additional electrical contacts in the computer housing 405 would be coupled to the processing unit 490 and the additional electrical contacts provided in battery recharger unit 480 would be coupled to a suitable cable that in turn would be coupled to a serial port, such as an RS R32 port or a USB port, of a device such as personal computer 35. This configuration thus provides an alternate method for uploading of data from and downloading of data to armband sensor device 400 using a physical connection.

FIG. 20 is a schematic diagram that shows the system architecture of armband sensor device 400, and in particular each of the components that is either on or coupled to PCB 445.

As shown in FIG. 17, PCB 445 includes processing unit 490, which may be a microprocessor, a microcontroller, or any other processing device that can be adapted to perform the functionality described herein. Processing unit 490 is adapted to provide all of the functionality described in connection with microprocessor 20 shown in FIG. 2. A suitable example of processing unit 490 is the Dragonball EZ sold by Motorola, Inc. of Schaumburg, Ill. PCB 445 also has thereon a two-axis accelerometer 495, a suitable example of which is the Model ADXL210 accelerometer sold by Analog Devices, Inc. of Norwood, Mass. Two-axis accelerometer 495 is preferably mounted on PCB 445 at an angle such that its sensing axes are offset at an angle substantially equal to 45 degrees from the longitudinal axis of PCB 445 and thus the longitudinal axis of the wearer's arm when armband sensor device 400 is worn. The longitudinal axis of the wearer's arm refers to the axis defined by a straight line drawn from the wearer's shoulder to the wearer's elbow. The output signals of two-axis accelerometer 495 are passed through buffers 500 and input into analog to digital converter 505 that in turn is coupled to processing unit 490. GSR sensors 465 are coupled to amplifier 510 on PCB 445. Amplifier 510 provides amplification and low pass filtering functionality, a suitable example of which is the Model AD8544 amplifier sold by Analog Devices, Inc. of Norwood, Mass. The amplified and filtered signal output by amplifier 510 is input into amp/offset 515 to provide further gain and to remove any bias voltage and into filter/conditioning circuit 520, which in turn are each coupled to analog to digital converter 505. Heat flux sensor 460 is coupled to differential input amplifier 525, such as the Model INA amplifier sold by Burr-Brown Corporation of Tucson, Ariz., and the resulting amplified signal is passed through filter circuit 530, buffer 535 and amplifier 540 before being input to analog to digital converter 505. Amplifier 540 is configured to provide further gain and low pass filtering, a suitable example of which is the Model AD8544 amplifier sold by Analog Devices, Inc. of Norwood, Mass. PCB 445 also includes thereon a battery monitor 545 that monitors the remaining power level of rechargeable battery 450. Battery monitor 545 preferably comprises a voltage divider with a low pass filter to provide average battery voltage. When a user depresses button 470 in the manner adapted for requesting battery level, processing unit 490 checks the output of battery monitor 545 and provides an indication thereof to the user, preferably through LEDs 475, but also possibly through vibrating motor 455 or ringer 575. An LCD may also be used.

PCB 445 may include three-axis accelerometer 550 instead of or in addition to two-axis accelerometer 495. The three-axis accelerometer outputs a signal to processing unit 490. A suitable example of three-axis accelerometer is the μPAM product sold by I.M. Systems, Inc. of Scottsdale, Ariz. Three-axis accelerometer 550 is preferably tilted in the manner described with respect to two-axis accelerometer 495.

PCB 445 also includes RF receiver 555 that is coupled to processing unit 490. RF receiver 555 may be used to receive signals that are output by another device capable of wireless transmission, shown in FIG. 20 as wireless device 558, worn by or located near the individual wearing armband sensor device 400. Located near as used herein means within the transmission range of wireless device 558. For example, wireless device 558 may be a chest mounted heart rate monitor such as the Tempo product sold by Polar Electro of Oulu, Finland. Using such a heart rate monitor, data indicative of the wearer's heart rate can be collected by armband sensor device 400. Antenna 560 and RF transceiver 565 are coupled to processing unit 490 and are provided for purposes of uploading data to central monitoring unit 30 and receiving data downloaded from central monitoring unit 30. RF transceiver 565 and RF receiver 555 may, for example, employ Bluetooth technology as the wireless transmission protocol. Also, other forms of wireless transmission may be used, such as infrared transmission.

The fact that RF Transceiver 565 may be used for wirelessly uploading data from and wirelessly downloading data to armband sensor device 400 is advantageous because it eliminates the need to remove armband sensor device 400 to perform these functions, as would be required with a physical connection. For example, if armband sensor device 400 was being worn under the user's clothing, requiring removal of armband sensor device 400 prior to uploading and/or downloading data increases user inconvenience. In addition, the wearing of armband sensor device 400 has an effect on the user's skin and underlying blood vessels, which in turn may effect any measurements being made with respect thereto. It may be necessary for a period of time during which armband sensor device 400 is worn by the user to elapse before a steady state is achieved and consistent, accurate measurements can be made. By providing armband sensor device 400 with wireless communications capability, data can be uploaded and downloaded without disturbing an established steady state equilibrium condition. For example, programming data for processing unit 490 that controls the sampling characteristics of armband sensor device 400 can be downloaded to armband sensor device 400 without disturbing the steady state equilibrium condition.

In addition, antenna 560 and RF transceiver 565 permit armband sensor device 400 to communicate wirelessly with other devices capable of wireless communication, i.e., transmit information to and receive information from those devices. The devices may include, for example, devices that are implanted in the body of the person using armband sensor device 400, such as an implantable heart pacemaker or an implantable insulin dispensing device, for example the MiniMed® 2007 implantable insulin pump sold by MiniMed Inc. of Northridge, Calif., devices worn on the body of the person using armband sensor device 400, or devices located near the person using armband sensor device 400 at any particular time, such as an electronic scale, a blood pressure monitor, a glucose monitor, a cholesterol monitor or another armband sensor device 400. With this two-way wireless communication capability, armband sensor device 400 may be adapted to transmit information that activates or deactivates such a device for use or information that programs such a device to behave in a particular way. For example, armband sensor device 400 may be adapted to activate a piece of exercise equipment such as a treadmill and program it to operate with certain parameters that are dictated or desired by or optimal for the user of armband sensor device 400. As another example, armband sensor device 400 may be adapted to adjust a computer controlled thermostat in a home based on the detected skin temperature of the wearer or turn off a computer controlled lighting system, television or stereo when the wearer is determined to have fallen asleep.

Vibrating motor 455 is coupled to processing unit 490 through vibrator driver 570 and provides tactile feedback to the wearer. Similarly, ringer 575, a suitable example of which is the Model SMT916A ringer sold by Projects Unlimited, Inc. of Dayton, Ohio, is coupled to processing unit 490 through ringer driver 580, a suitable example of which is the Model MMBTA14 CTI darlington transistor driver sold by Motorola, Inc. of Schaumburg, Ill., and provides audible feedback to the wearer. Feedback may include, for example, celebratory, cautionary and other threshold or event driven messages, such as when a wearer reaches a level of calories burned during a workout.

Also provided on PCB 445 and coupled to processing unit 490 is momentary switch 585. Momentary switch 585 is also coupled to button 470 for activating momentary switch 585. LEDs 475, used to provide various types of feedback information to the wearer, are coupled to processing unit 490 through LED latch/driver 590.

Oscillator 595 is provided on PCB 445 and supplies the system clock to processing unit 490. Reset circuit 600, accessible and triggerable through a pin-hole in the side of computer housing 405, is coupled to processing unit 490 and enables processing unit 490 to be reset to a standard initial setting.

Rechargeable battery 450, which is the main power source for the armband sensor device 400, is coupled to processing unit 490 through voltage regulator 605. Finally, memory functionality is provided for armband sensor device 400 by SRAM 610, which stores data relating to the wearer of armband sensor device 400, and flash memory 615, which stores program and configuration data, provided on PCB 445. SRAM 610 and flash memory 615 are coupled to processing unit 490 and each preferably have at least 512K of memory.

In manufacturing and assembling armband sensor device 400, top portion 435 of computer housing 405 is preferably formed first, such as by a conventional molding process, and flexible wing body 410 is then overmolded on top of top portion 435. That is, top portion 435 is placed into an appropriately shaped mold, i.e., one that, when top portion 435 is placed therein, has a remaining cavity shaped according to the desired shape of flexible wing body 410, and flexible wing body 410 is molded on top of top portion 435. As a result, flexible wing body 410 and top portion 435 will merge or bond together, forming a single unit. Alternatively, top portion 435 of computer housing 405 and flexible wing body 410 may be formed together, such as by molding in a single mold, to form a single unit. The single unit however formed may then be turned over such that the underside of top portion 435 is facing upwards, and the contents of computer housing 405 can be placed into top portion 435, and top portion 435 and bottom portion 440 can be affixed to one another. As still another alternative, flexible wing body 410 may be separately formed, such as by a conventional molding process, and computer housing 405, and in particular top portion 435 of computer housing 405, may be affixed to flexible wing body 410 by one of several known methods, such as by an adhesive, by snap-fitting, or by screwing the two pieces together. Then, the remainder of computer housing 405 would be assembled as described above. It will be appreciated that rather than assembling the remainder of computer housing 405 after top portion 435 has been affixed to flexible wing body 410, the computer housing 405 could be assembled first and then affixed to flexible wing body 410.

Figure 21:
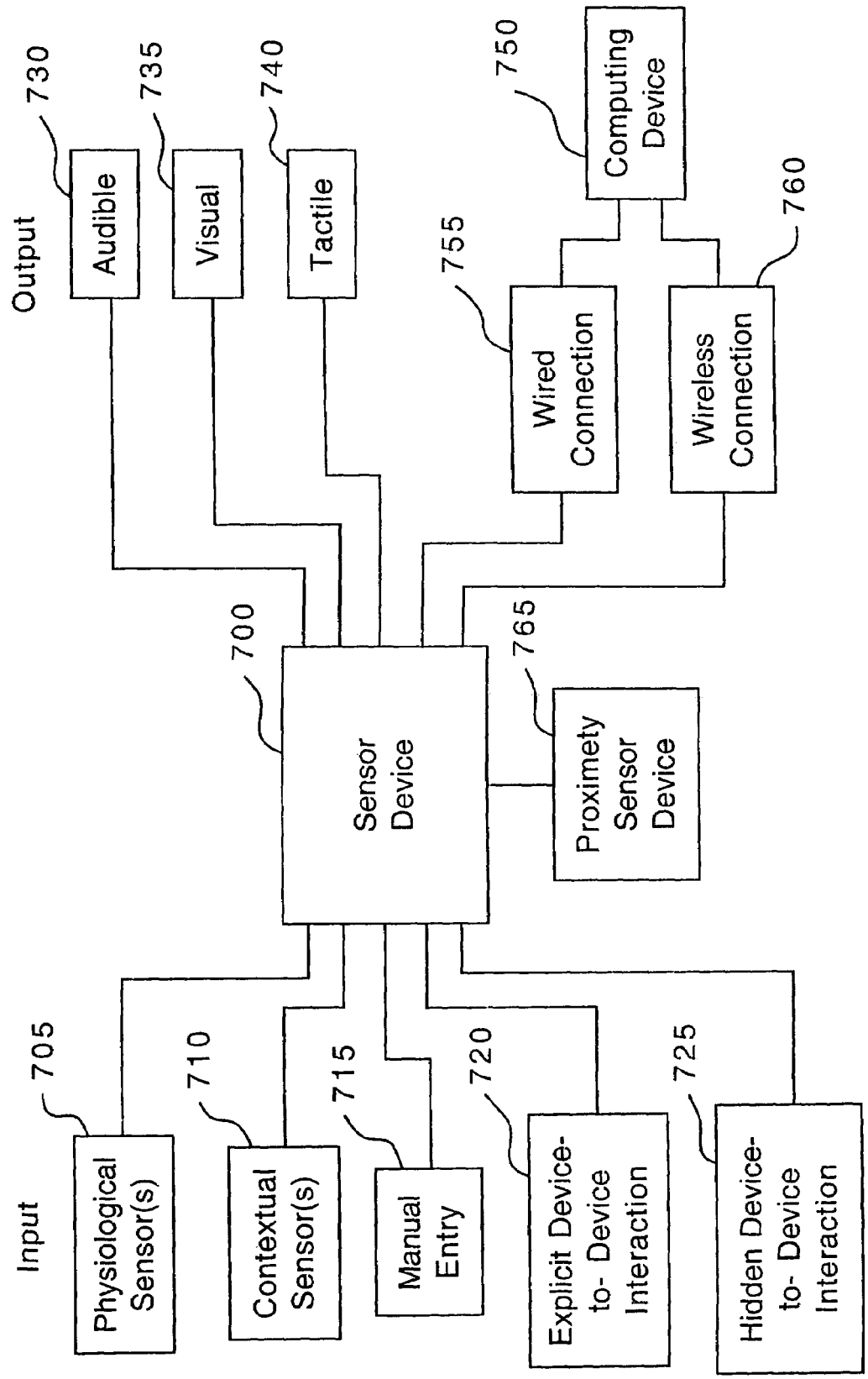
FIG. 21 is a block diagram of an apparatus for monitoring health, wellness and fitness according to an alternate embodiment of the present invention.

Referring to FIG. 21, a block diagram of an alternate embodiment of the present invention is shown. This alternate embodiment includes stand alone sensor device 700 which functions as an independent device, meaning that it is capable of collecting and/or generating the various types of data described herein in connection with sensor device 10 and sensor device 400 and providing analytical status data to the user without interaction with a remotely located apparatus such as central monitoring unit 30. Stand alone sensor device 700 includes a processor that is programmed and/or otherwise adapted to include the utilities and algorithms necessary to create analytical status data from the data indicative of various physiological and/or contextual parameters of the user, the data derived therefrom, and the data input by the user, all of which is stored in and accessed as needed from memory provided in stand alone sensor device 700. Stand alone sensor device 700 may comprise sensor device 10 shown in FIGS. 1 and 2 that includes microprocessor 20 and memory 22 or armband sensor device 400 shown in FIGS. 12-17 that includes processing unit 490 and SRAM 610.

As shown schematically in FIG. 21, data may be input into stand alone sensor device 700 in a number of ways. Stand alone sensor device 700 may include one or more physiological sensors 705 as described herein for facilitating the collection of data indicative of various physiological parameters of the user. Stand alone sensor device 700 may also include one or more contextual sensors 710 as described herein for facilitating the collection of data indicative of various contextual parameters of the user. As indicated by reference number 715, stand alone sensor device 700 may be adapted to enable the manual entry of data by the user. For example, stand alone sensor device 700 may include a data input button, such as a button 470 of armband sensor device 400, through which a user could manually enter information such as information relating to various life activities of the user as described herein or information relating to the operation and/or control of stand alone sensor device 700, for example, the setting of reminders or alerts as described herein. In this example, activation of button 470 may simply record or time stamp that an event such as a meal has occurred, with the wearer needing to assign a meaning to that time stamp through data entry at a later time. Alternatively, activation of button 470 in certain sequences, such as one activation, two successive activations, three successive activations, etc., can be preset to have different specific meanings. A wearer would need to follow a menu or guide of such preset activation sequences to input relevant data. Alternatively, stand alone sensor device 700 may include a more sophisticated means for manual entry of information such as a keypad, a touch screen, a microphone, or a remote control device, for example a remote control device incorporated into a wristwatch. In the case of a microphone, the processor of stand alone sensor device 700 would be provided with well known voice recognition software or the like for converting the input speech into usable data.

As indicated by reference numbers 720 and 725, information comprising data indicative of various physiological and/or contextual parameters and data derived therefrom may be input into stand alone sensor device 700 through interaction with other devices. In addition, information such as handshake data or data indicative of various physiological and/or contextual parameters and data derived therefrom may be output from stand alone sensor device 700 to such other devices. According to one embodiment, the interaction is in the form of wireless communication between stand alone sensor device 700 and another device capable of wireless communication by way of a wireless transceiver provided in stand alone sensor device 700, such as wireless transceiver 565 shown and described in connection with FIG. 20. The device-to-device interaction may, as shown by reference number 720, be explicit, meaning that the user of stand alone sensor device 700 has knowingly initiated the interaction. For example, a user may activate a button on a scale to upload data to stand alone sensor device 700. The device-to-device interaction may also, as shown by reference number 725, be hidden, meaning that the user of stand alone sensor device 700 does not knowingly initiate the interaction. For example, a gym may have a sensor that wirelessly transmits a signal to sensing device 700 when the user enters and leaves the gym to time stamp when the user began and ended a workout.

As shown schematically in FIG. 21, information may be output or transmitted from stand alone sensor device 700 in a number of ways. Such information may include the data indicative of various physiological parameters and/or contextual parameters, the data derived therefrom, the data manually input by the user, the analytical status data, or any combination thereof. As shown by reference numbers 730, 735 and 740, information may be output or transmitted in an audible fashion such as by a series of tones or beeps or a recorded voice by a device such as a speaker, in a visual fashion such as by one or more LEDs, or in a tactile fashion such as by vibration. For example, stand alone sensor device 700 may be adapted to output a tone or tones, light an LED or LEDs, or vibrate as a reminder for an event, such as a reminder to eat or exercise at a particular time, or when a goal has been reached, such as a target number of calories burned during a workout, or a condition has been sensed, such as ovulation. Alternatively, stand alone sensor device 700 may be provided with a more sophisticated visual output means such as an LCD similar to those found on commercially available cell phones, pagers and personal digital assistants. With an LCD or a similar device and the expanded visual output capabilities it would provide, stand alone sensor device 700 may be adapted to output or transmit some or all of the information described in connection with FIGS. 5 through 11 in the same or a similar format. For example, stand alone sensor device 700 could provide analytical status data in the form of the Health Index to the user. As a further alternative, stand alone sensor device 700 may be coupled to computing device 750 such as a personal computer, a cell phone, a pager, a personal digital assistant, another stand alone sensor device 700 or any other device having a processor by either wired connection 755 or wireless connection 760. For example, battery recharger unit 480 shown in FIG. 19 may be used to provide the wired connection 755 or wireless connection 760. In this configuration, the display of the computing device could be used to visually output information from stand alone sensor device 700. It will be appreciated that since computing device 750 includes a sophisticated output means such as an LCD, it may be used to output or transmit to the user some or all of the information described in connection with FIGS. 5 through 11, such as the Health Index, in the same or a similar format.

Also, computing device 750 may in turn be used to control other devices, such as the lights or thermostat in a home, based on data output by stand alone sensor device 700, such as the fact that the wearer has fallen asleep or the fact that the wearer's skin temperature has reached a certain level. In other words, stand alone sensor device 700, and in particular its processor, may be adapted to cause a computing device 750 to trigger an event upon detection of one or more physiological and/or contextual conditions by stand alone sensor device 700. Alternatively, stand alone sensor device 700 may be adapted to cause a computing device 750 to trigger an event based upon information received from another computing device 750.

Stand alone sensor device 700 may be adapted to interact with and influence an interactive electronic media device, such as a video game, or non-interactive electronic media device, such as on a display device such as a DVD or digital video disc player playing a digitally recorded movie. For example, stand alone sensor device 700 may be adapted to transmit information relating to the physiological state of the wearer to the video game, which in turn adjusts the characteristics of the game, such as the level of difficulty. As another example, stand alone sensor device 700 may be adapted to transmit information relating to the physiological state of the wearer to the device displaying the digitally recorded movie which in turn adjusts the characteristics, such as the outcome, of the movie.

Furthermore, stand alone sensor device 700 may include location sensing device 765, such as an ultrasonic or a radio-frequency identification tag, for enabling a computing device 750 to detect the geographic location of stand alone sensor device 700, such as the location of stand alone sensor device 700 within a defined space such as a building. In one embodiment, a location indication causes computing device 750 to trigger an event, such as lowering the temperature in a room corresponding to the indicated location, preferably based on the detection by stand alone sensor device 700 of one or more physiological conditions of the wearer, such as skin temperature. In another embodiment, the location indication causes computing device 750 to trigger an event, such as lowering the temperature in a room corresponding to the indicated location, if stand alone sensor device 700 detects one or more physiological conditions, such as a skin temperature of the wearer being above a certain level. In addition, the input means of the computing device, such as the mouse and keyboard of a personal computer, the keypad of a cell phone or pager, or the touch screen of a personal digital assistant, may be used to manually input information into stand alone sensor device 700.

The different modes of output may be used in combination to provide different types and levels of information to a user. For example, stand alone sensor device 700 could be worn by an individual while exercising and an LED or a tone can be used to signal that a goal of a certain number of calories burned has been reached. The user could then transmit additional data wirelessly from stand alone sensor device 700 to a computing device 750 such as a cell phone after he or she is finished exercising to view data such as heart rate and/or respiration rate over time.

As a further alternative embodiment of the present invention, rather than the processor provided in stand alone sensor device 700 being programmed and/or otherwise adapted to generate the derived data and to include the utilities and algorithms necessary to create analytical status data, computing device 750 could be so programmed. In this embodiment, stand alone sensor device 700 collects and/or generates the data indicative of various physiological and/or contextual parameters of the user, the data manually input by the user, and/or data input as a result of device-to-device interaction shown at 720 and 725, all of which is stored in the memory provided in stand alone sensor device 700. This data is then periodically uploaded to computing device 750 which in turn generates derived data and/or analytical status data. Alternatively, the processor of stand alone sensor device 700 could be programmed to generate the derived data with computing device 750 being programmed and/or otherwise adapted to include the utilities and algorithms necessary to create analytical status data based on data indicative of one or more physiological and/or contextual parameters, data derived therefrom, data manually input by the user and/or data input as a result of device-to-device interaction shown at 720 and 725 uploaded from stand alone sensor device 700. As still a further alternative, the processor of stand alone sensor device 700 could be programmed and/or otherwise adapted to include the utilities and algorithms necessary to create analytical status data based on data indicative of one or more physiological and/or contextual parameters, data derived therefrom, data manually input by the user and/or data input as a result of device-to-device interaction shown at 720 and 725 uploaded from stand alone sensor device 700 with computing device 750 being programmed to generate the derived data. In either alternative, any or all of the data indicative of physiological and/or contextual parameters of the user, the data derived therefrom, the data manually input by the user, the data input as a result of device-to-device interaction shown at 720 and 725 and the analytical status data may then be viewed by the user using the output means of the programmed computing device 750 or another computing device 750 to which the data is downloaded. In the latter alternative, everything but the analytical status data may also be output by stand alone sensor device 700 as described herein.

Computing device 750 in these alternative embodiments may be connected to an electronic network, such as the Internet, to enable it to communicate with central monitoring unit 30 or the like. The programming of computing device 750 that enables it to generate the derived data and/or the analytical status data may, with such a configuration, be modified or replaced by downloading the relevant data to computing device 750 over the electronic network.

As still a further alternative embodiment, computing device 750 may be provided with a custom written plug-in adapted to provide data display functionality through use of a well known browser program. In this embodiment, stand alone sensor device 700 collects and/or generates the data indicative of various physiological and/or contextual parameters of the user, the derived data, the data input by the user, data input as a result of device-to-device interaction shown at 720 and 725, and/or analytical status data based thereon and uploads this data to computing device 750. The plug-in provided in computing device 750 then generates appropriate display pages based on the data which maybe viewed by the user using the browser provided with computing device 750. The plug-in may be modified/updated from a source such as central monitoring unit 30 over an electronic network such as the Internet.

The terms and expressions which have been employed herein are used as terms of description and not as limitation, and there is no intention in the use of such terms and expressions of excluding equivalents of the features shown and described or portions thereof, it being recognized that various modifications are possible within the scope of the invention claimed. Although particular embodiments of the present invention have been illustrated in the foregoing detailed description, it is to be further understood that the present invention is not to be limited to just the embodiments disclosed, but that they are capable of numerous rearrangements, modifications and substitutions.

What is claimed is:

1. An apparatus for detecting, monitoring and reporting human status information, comprising:
    at least two sensors selected from the group consisting of physiological sensors and contextual sensors, said sensors generating data of a first parameter and a second parameter of an individual and said sensors generating data during non-sedentary activities;
    a processor in electronic communication with said at least two sensors, said processor generating (a) derived data based on said data of a first parameter and a second parameter, said derived data comprising a third parameter of said individual, and (b) analytical status data from at least a portion of at least one of (i) said data of a first parameter, (ii) said data of a second parameter, and (iii) said derived data; and
    means for transmitting to said individual at least one of said data of a first parameter and a second parameter said derived data and said analytical status data,
    wherein said third parameter comprises caloric expenditure data; and
    wherein said first and second parameters are produced by at least one of said individual's body and the environment adjacent to said individual's body.

2. An apparatus according to claim 1, further comprising a wireless transceiver for receiving information from and transmitting information to at least one of a wireless device worn by said individual, a wireless device implanted in the body of said individual, and a wireless device located near said individual.

3. An apparatus according to claim 2, said information received by said wireless transceiver comprising at least one of data indicative of a physiological parameter of said individual and data derived therefrom.

4. An apparatus according to claim 1, further comprising means for receiving information from and transmitting information to at least one of a wireless device worn by said individual, a wireless device implanted in the body of said individual, and a wireless device located near said individual.

5. An apparatus according to claim 1, further comprising a wireless communication component for receiving information from at least one of a wireless device worn by said individual, a wireless device implanted in the body of said individual, and a wireless device located near said individual.

6. An apparatus according to claim 1, said means for transmitting further comprising a computing device in electronic communication with said processor.

7. An apparatus according to claim 6, said computing device being coupled to said processor by a physical connection.

8. An apparatus according to claim 6, said computing device being coupled to said processor by a wireless connection.

9. An apparatus according to claim 1, further comprising means for manually entering information into said apparatus.

10. An apparatus according to claim 9, said manually entered information being stored in a memory.

11. An apparatus according to claim 9, said analytical status data being generated from at least a portion of said manually entered information.

12. An apparatus according to claim 1, further comprising a manual input device for manually inputting information into said apparatus.

13. An apparatus according to claim 12, said manually input information being stored in a memory.

14. An apparatus according to claim 12, said analytical status data being generated from at least a portion of said manually input information.

15. An apparatus according to claim 1, said means for transmitting comprising a visual output device.

16. An apparatus according to claim 1, said means for transmitting comprising an audible output device.

17. An apparatus according to claim 1, said means for transmitting comprising a tactile output device.

18. An apparatus according to claim 1, said means for transmitting comprising a computing device coupled to said processor, said processor being adapted to cause said computing device to trigger an event upon detection of one or more physiological conditions of said individual.

19. An apparatus according to claim 1, said processor being adapted to cause a computing device to trigger an event upon detection of one or more physiological conditions of said individual.

20. An apparatus according to claim 1, said apparatus further comprising a location sensing device for indicating to a computing device a location of said apparatus within a defined space.

21. An apparatus according to claim 20, wherein an indication of a location of said apparatus within a defined space causes said computing device to trigger an event.

22. An apparatus according to claim 21, said event being based on one or more physiological conditions of said individual detected by said apparatus.

23. An apparatus according to claim 20, wherein an indication of a location of said apparatus causes said computing device to trigger an event if said apparatus detects one or more physiological conditions of said individual.

24. An apparatus according to claim 9, said apparatus monitoring the degree to which said individual has followed a predetermined routine, said analytical status data comprising feedback to said individual relating to the degree to which said individual has followed said predetermined routine, said feedback being generated from at least a portion of at least one of said data of a first parameter, said data of a second parameter, said derived data, and said manually entered data.

25. An apparatus according to claim 12, said apparatus monitoring the degree to which said individual has followed a predetermined routine, said analytical status data comprising feedback to said individual relating to the degree to which said individual has followed said predetermined routine, said feedback being generated from at least a portion of at least one of said data of a first parameter, said data of a second parameter, said derived data and said manually input data.

26. An apparatus according to claim 24, wherein said routine comprises a plurality of categories and said feedback is generated and provided with respect to each of said categories.

27. An apparatus according to claim 25, wherein said routine comprises a plurality of categories and said feedback is generated and provided with respect to each of said categories.

28. An apparatus according to claim 26, wherein said categories include two or more of nutrition, activity level, mind centering, sleep, and daily activities.

29. An apparatus according to claim 27, wherein said categories include two or more of nutrition, activity level, mind centering, sleep, and daily activities.

30. An apparatus according to claim 28, wherein at least a portion of said feedback is in at least one of graphical and textual form.

31. An apparatus according to claim 29, wherein at least a portion of said feedback is in at least one of graphical and textual form.

32. An apparatus for detecting, monitoring and reporting human status information, comprising:
a sensor device including:
at least two sensors selected from the group consisting of physiological sensors and contextual sensors, said sensors generating data of a first parameter and a second parameter of an individual and said sensors generating data during non-sedentary activities, wherein said first and second parameters are produced by at least one of said individual's body and the environment adjacent to said individual's body; and
at least one of a computing device and a processor in electronic communication with said sensor device, said at least one of a computing device and processor generating derived data based on said data of a first parameter and a second parameter, said derived data comprising a third parameter of said individual, said third parameter being an individual status parameter that cannot be directly detected by any of said at least two sensors and said third parameter comprises caloric expenditure data.

33. An apparatus according to claim 32, said sensor device further comprising a wireless transceiver for receiving information from and transmitting information to at least one of a wireless device worn by said individual, a wireless device implanted in the body of said individual, and a wireless device located near said individual.

34. An apparatus according to claim 33, said information received by said wireless transceiver comprising at least one of data indicative of a physiological parameter of said individual and data derived therefrom.

35. An apparatus according to claim 32, said sensor device further comprising means for receiving information from and transmitting information to at least one of a wireless device worn by said individual, a wireless device implanted in the body of said individual, and a wireless device located near said individual.

36. An apparatus according to claim 32, further comprising a wireless communication component for receiving information from at least one of a wireless device worn by said individual, a wireless device implanted in the body of said individual, and a wireless device located near said individual.

37. An apparatus according to claim 32, said sensor device further comprising means for transmitting to said individual at least one of said data of a first parameter and a second parameter and said derived data.

38. An apparatus according to claim 37, said means for transmitting comprising a visual output device.

39. An apparatus according to claim 37, said means for transmitting comprising an audible output device.

40. An apparatus according to claim 37, said means for transmitting comprising a tactile output device.

41. An apparatus according to claim 32, said computing device being adapted to output to said individual at least one of said data of a first parameter and a second parameter and said derived data.

42. An apparatus according to claim 32, said computing device being coupled to said sensor device by a physical connection.

43. An apparatus according to claim 32, said computing device being coupled to said sensor device by a wireless connection.

44. An apparatus according to claim 32, said sensor device further comprising means for manually entering information into said apparatus.

45. An apparatus according to claim 44, said manually entered information being stored in a memory.

46. An apparatus according to claim 44, wherein analytical status data is generated from at least a portion of said manually entered information.

47. An apparatus according to claim 32, further comprising a manual input device for manually inputting information into said apparatus.

48. An apparatus according to claim 47, said manually input information being stored in a memory.

49. An apparatus according to claim 47, wherein analytical status data is generated from at least a portion of said manually input information.

50. An apparatus according to claim 32, said apparatus being adapted to cause a second computing device to trigger an event upon detection of one or more physiological conditions of said individual.

51. An apparatus according to claim 32, said apparatus further comprising a location sensing device for indicating to a second computing device a location of said apparatus within a defined space.

52. An apparatus according to claim 51, wherein an indication of a location of said apparatus within a defined space causes said second computing device to trigger an event.

53. An apparatus according to claim 52, said event being based on one or more physiological conditions of said individual detected by said apparatus.

54. An apparatus according to claim 51, wherein an indication of a location of said apparatus within a defined space causes said second computing device to trigger an event if said apparatus detects one or more physiological conditions of said individual.

55. An apparatus according to claim 44, said apparatus monitoring the degree to which said individual has followed a predetermined routine, wherein analytical status data comprising feedback to said individual relating to the degree to which said individual has followed said predetermined routine is generated, said feedback being generated from at least a portion of at least one of said data of a first parameter, said data of a second parameter, said derived data and said manually entered data.

56. An apparatus according to claim 47, said apparatus monitoring the degree to which said individual has followed a predetermined routine, wherein analytical status data comprising feedback to said individual relating to the degree to which said individual has followed said predetermined routine is generated, said feedback being generated from at least a portion of at least one of said data of a first parameter, said data of a second parameter, said derived data and said manually input data.

57. An apparatus according to claim 55, wherein said routine comprises a plurality of categories and said feedback is generated and provided with respect to each of said categories.

58. An apparatus according to claim 56, wherein said routine comprises a plurality of categories and said feedback is generated and provided with respect to each of said categories.

59. An apparatus according to claim 57, wherein said categories include two or more of nutrition, activity level, mind centering, sleep, and daily activities.

60. An apparatus according to claim 58, wherein said categories include two or more of nutrition, activity level, mind centering, sleep, and daily activities.

61. An apparatus according to claim 59, wherein at least a portion of said feedback is in at least one of graphical and textual form.

62. An apparatus according to claim 60, wherein at least a portion of said feedback is in at least one of graphical and textual form.

63. An apparatus for detecting, monitoring and reporting human status information, comprising:
a sensor device including:
at least two sensors selected from the group consisting of physiological sensors and contextual sensors, said sensors generating data of a first parameter and a second parameter of an individual and said sensors generating data during non-sedentary activities;
a processor in electronic communication with said at least two sensors, said processor generating derived data based on said data indicative of a first parameter and a second parameter, said derived data comprising a third parameter of said individual; and
a computing device in electronic communication with at least one of said processor and said sensor device, said computing device generating analytical status data from at least a portion of at least one of said data indicative of a first parameter, said data indicative of a second parameter and said derived data,
wherein said third parameter comprises caloric expenditure data; and
wherein said first and second parameters are produced by at least one of said individual's body and the environment adjacent to said individual's body.

64. An apparatus according to claim 63, said sensor device further comprising a wireless transceiver for receiving information from and transmitting information to at least one of a wireless device worn by said individual, a wireless device implanted in the body of said individual, and a wireless device located near said individual.

65. An apparatus according to claim 64, said information received by said wireless transceiver comprising at least one of data indicative of a physiological parameter of said individual and data derived therefrom.

66. An apparatus according to claim 63, said sensor device farther comprising means for receiving information from and transmitting information to at least one of a wireless device worn by said individual, a wireless device implanted in the body of said individual, and a wireless device located near said individual.

67. An apparatus according to claim 63, further comprising a wireless communication component for receiving information from at least one of a wireless device worn by said individual, a wireless device implanted in the body of said individual, and a wireless device located near said individual.

68. An apparatus according to claim 63, said sensor device further comprising means for transmitting to said individual at least one of said data of a first parameter and a second parameter, said derived data and said analytical status data.

69. An apparatus according to claim 68, said means for transmitting comprising a visual output device.

70. An apparatus according to claim 68, said means for transmitting comprising an audible output device.

71. An apparatus according to claim 68, said means for transmitting comprising a tactile output device.

72. An apparatus according to claim 63, said computing device being adapted to output to said individual at least one of said data of a first parameter and a second parameter, said derived data and said analytical status data.

73. An apparatus according to claim 63, said computing device being coupled to said sensor device by a physical connection.

74. An apparatus according to claim 63, said computing device being coupled to said sensor device by a wireless connection.

75. An apparatus according to claim 63, said sensor device further comprising means for manually entering information into said apparatus.

76. An apparatus according to claim 75, said manually entered information being stored in a memory.

77. An apparatus according to claim 75, said analytical status data being generated from at least a portion of said manually entered information.

78. An apparatus according to claim 63, further comprising a manual input device for manually inputting information into said apparatus.

79. An apparatus according to claim 78, said manually input information being stored in a memory.

80. An apparatus according to claim 78, said analytical status data being generated from at least a portion of said manually input information.

81. An apparatus according to claim 63, said processor being adapted to cause a second computing device to trigger an event upon detection of one or more physiological conditions of said individual.

82. An apparatus according to claim 63, said apparatus further comprising a location sensing device for indicating to a second computing device a location of said apparatus within a defined space.

83. An apparatus according to claim 82, wherein an indication of a location of said apparatus within a defined space causes said second computing device to trigger an event.

84. An apparatus according to claim 83, said event being based on one or more physiological conditions of said individual detected by said apparatus.

85. An apparatus according to claim 82, wherein an indication of a location of said apparatus within a defined space causes said second computing device to trigger an event if said apparatus detects one or more physiological conditions of said individual.

86. An apparatus according to claim 75, said apparatus monitoring the degree to which said individual has followed a predetermined routine, said analytical status data comprising feedback to said individual relating to the degree to which said individual has followed said predetermined routine, said feedback being generated from at least a portion of at least one of said data of a first parameter, said data of a second parameter, said derived data and said manually entered data.

87. An apparatus according to claim 78, said apparatus monitoring the degree to which said individual has followed a predetermined routine, said analytical status data comprising feedback to said individual relating to the degree to which said individual has followed said predetermined routine, said feedback being generated from at least a portion of at least one of said data of a first parameter, said data of a second parameter, said derived data and said manually input data.

88. An apparatus according to claim 86, wherein said routine comprises a plurality of categories and said feedback is generated and provided with respect to each of said categories.

89. An apparatus according to claim 87, wherein said routine comprises a plurality of categories and said feedback is generated and provided with respect to each of said categories.

90. An apparatus according to claim 88, wherein said categories include two or more of nutrition, activity level, mind centering, sleep, and daily activities.

91. An apparatus according to claim 89, wherein said categories include two or more of nutrition, activity level, mind centering, sleep, and daily activities.

92. An apparatus according to claim 90, wherein at least a portion of said feedback is in at least one of graphical and textual form.

93. An apparatus according to claim 91, wherein at least a portion of said feedback is in at least one of graphical and textual form.

94. An apparatus for detecting, monitoring and reporting human status information, comprising:
 a sensor device including:
  at least two sensors selected from the group consisting of physiological sensors and contextual sensors, said sensors generating data of a first parameter and a second parameter of an individual and generating data during non-sedentary activities;
  a processor in electronic communication with said sensor device generating derived data from said data of a first parameter and said data of a second parameter, said derived data comprising a third parameter of said individual; and
  a memory for retrievably storing at least one of said data of a first parameter, said data of a second parameter and said derived data; and
  a computing device in electronic communication with at least one of said processor, said memory and said sensor device, said computing device capable of further generating derived data from at least one of said data of a first parameter, said data of a second parameter and said data derived by said processor, said computing comprising graphical utility graphically displaying any of said derived data in relation to at least one of said of a first parameter, said data of a second parameter, and any of said derived data,
 wherein said third parameter comprises caloric expenditure data; and
 wherein said first and second parameters are produced by at least one of said individual's body and the environment adjacent to said individuals body.

95. An apparatus according to claim 94, said sensor device further comprising a wireless transceiver for receiving information from and transmitting information to at least one of a wireless device worn by said individual, a wireless device implanted in the body of said individual, and a wireless device located near said individual.

96. An apparatus according to claim 95, said information received by said wireless transceiver comprising at least one of data indicative of a physiological parameter of said individual and data derived therefrom.

97. An apparatus according to claim 94, said sensor device further comprising means for receiving information from and transmitting information to at least one of a wireless device worn by said individual, a wireless device implanted in the body of said individual, and a wireless device located near said individual.

98. An apparatus according to claim 94, further comprising a wireless communication component for receiving information from at least one of a wireless device worn by said individual, a wireless device implanted in the body of said individual, and a wireless device located near said individual.

99. An apparatus according to claim 94, said sensor device further comprising means for transmitting to said individual at least one of said data of a first parameter and a second parameter, and said derived data.

100. An apparatus according to claim 99, said means for transmitting comprising a visual output device.

101. An apparatus according to claim 99, said means for transmitting comprising an audible output device.

102. An apparatus according to claim 99, said means for transmitting comprising a tactile output device.

103. An apparatus according to claim 94, said computing device being adapted to output to said individual at least one of said data of a first parameter and a second parameter, and said derived data.

104. An apparatus according to claim 94, said computing device being coupled to said sensor device by a physical connection.

105. An apparatus according to claim 94, said computing device being coupled to said sensor device by a wireless connection.

106. An apparatus according to claim 94, said sensor device further comprising means for manually entering information into said apparatus.

107. An apparatus according to claim 106, said manually entered information being stored in said memory.

108. An apparatus according to claim 106, wherein analytical status data is generated from at least a portion of said manually entered information.

109. An apparatus according to claim 94, further comprising a manual input device for manually inputting information into said apparatus.

110. An apparatus according to claim 109, said manually input information being stored in said memory.

111. An apparatus according to claim 109, wherein analytical status data is generated from at least a portion of said manually input information.

112. An apparatus according to claim 94, said processor being adapted to cause a second computing device to trigger an event upon detection of one or more physiological conditions of said individual.

113. An apparatus according to claim 94, said apparatus further comprising a location sensing device for indicating to a second computing device a location of said apparatus within a defined space.

114. An apparatus according to claim 113, wherein an indication of a location of said apparatus within a defined space causes said second computing device to trigger an event.

115. An apparatus according to claim 114, said event being based on one or more physiological conditions of said individual detected by said apparatus.

116. An apparatus according to claim 114, wherein the indication of the location of said apparatus within a defined space causes said second computing device to trigger an event if said apparatus detects one or more physiological conditions of said individual.

117. An apparatus according to claim 106, said apparatus monitoring the degree to which said individual has followed a predetermined routine, wherein analytical status data comprising feedback to said individual relating to the degree to which said individual has followed said predetermined routine is generated, said feedback being generated from at least a portion of at least one of said data of a first parameter, said data of a second parameter, said derived data and said manually entered data.

118. An apparatus according to claim 109, said apparatus monitoring the degree to which said individual has followed a predetermined routine, wherein analytical status data comprising feedback to said individual relating to the degree to which said individual has followed said predetermined routine is generated, said feedback being generated from at least a portion of at least one of said data of a first parameter, said data of a second parameter, said derived data and said manually input data.

119. An apparatus according to claim 117, wherein said routine comprises a plurality of categories and said feedback is generated and provided with respect to each of said categories.

120. An apparatus according to claim 118, wherein said routine comprises a plurality of categories and said feedback is generated and provided with respect to each of said categories.

121. An apparatus according to claim 119, wherein said categories include two or more of nutrition, activity level, mind centering, sleep, and daily activities.

122. An apparatus according to claim 120, wherein said categories include two or more of nutrition, activity level, mind centering, sleep, and daily activities.

123. An apparatus according to claim 121, wherein at least a portion of said feedback is in at least one of graphical and textual form.

124. An apparatus according to claim 122, wherein at least a portion of said feedback is in at least one of graphical and textual form.

125. An apparatus according to claim 1, said apparatus further comprising a location sensing device for indicating to a computing device a geographic location of said apparatus.

126. An apparatus according to claim 125, wherein an indication of geographic location causes said computing device to trigger an event.

127. An apparatus according to claim 32 said apparatus further comprising a location sensing device for indicating to a second computing device a geographic location of said apparatus.

128. An apparatus according to claim 127, wherein an indication of geographic location causes said second computing device to trigger an event.

129. An apparatus according to claim 63, said apparatus further comprising a location sensing device for indicating to a second computing device a geographic location of said apparatus.

130. An apparatus according to claim 129, wherein an indication of geographic location causes said second computing device to trigger an event.

131. An apparatus according to claim 94, said apparatus further comprising a location sensing device for indicating to a second computing device a geographic location of said apparatus.

132. An apparatus according to claim 131, wherein an indication of geographic location causes said second computing device to trigger an event.

133. An apparatus according to claim 1, further comprising a wireless communication component for transmitting information to at least one of a wireless device worn by said individual, a wireless device implanted in the body of said individual, and a wireless device located near said individual.

134. An apparatus according to claim 32, further comprising a wireless communication component for transmitting information to at least one of a wireless device worn by said individual, a wireless device implanted in the body of said individual, and a wireless device located near said individual.

135. An apparatus according to claim 63, further comprising a wireless communication component for transmitting information to at least one of a wireless device worn by said individual, a wireless device implanted in the body of said individual, and a wireless device located near said individual.

136. An apparatus according to claim 94, further comprising a wireless communication component for transmitting information to at least one of a wireless device worn by said individual, a wireless device implanted in the body of said individual, and a wireless device located near said individual.

137. An apparatus according to claim 1, said apparatus being adapted to receive information from said processor and cause a computing device to trigger an event based on said received information.

138. An apparatus according to claim 32, said apparatus being adapted to communicate information from at least one of said computing device and said processor and cause a second computing device to trigger an event based on said received information.

139. An apparatus according to claim 63, said apparatus being adapted to receive information from said computing device and cause a second computing device to trigger an event based on said received information.

140. An apparatus according to claim 94, said apparatus being adapted to receive information from said computing device and cause a second computing device to trigger an event based on said received information.

141. An apparatus according to claim 1, further comprising a wireless communication component for transmitting at least one of said data of a first parameter, said data of a second parameter, said derived data and said analytical status data to an electronic media device, said electronic media device including electronic media, the transmitted at least one of said data of a first parameter, said data of a second parameter, said derived data and said analytical status data being used to adjust one or more characteristics of said electronic media.

142. An apparatus according to claim 32, further comprising a wireless communication component for transmitting at least one of said data of a first parameter, said data of a second parameter, said derived data to an electronic media device, said electronic media device including electronic media, the transmitted at least one of said data of a first parameter, said data of a second parameter, said derived data being used to adjust one or more characteristics of said electronic media.

143. An apparatus according to claim 63, further comprising a wireless communication component for transmitting at least one of said data of a first parameter, said data of a second parameter, said derived data and said analytical status data to an electronic media device, said electronic media device including electronic media, the transmitted at least one of said data of a first parameter, said data of a second parameter, said derived data and said analytical status data being used to adjust one or more characteristics of said electronic media.

144. An apparatus according to claim 94, further comprising a wireless communication component for transmitting at least one of said data of a first parameter, said data of a second parameter, said derived data to an electronic media device, said electronic media device including electronic media, the transmitted at least one of said data of a first parameter, said data indicative of a second parameter, said derived data being used to adjust one or more characteristics of said electronic media.

145. An apparatus according to claim 94, said apparatus monitoring the degree to which said individual has achieved one or more nutritional goals, wherein analytical status data comprising feedback to said individual relating to the degree to which said individual has achieved said one or more nutritional goals is generated, said feedback being generated from at least a portion of said nutritional information.

146. An apparatus according to claim 95, wherein at least a portion of said feedback is in graphical form.

* * * * *